United States Patent [19]

Miyoshi et al.

[11] Patent Number: 4,667,025
[45] Date of Patent: May 19, 1987

[54] OLIGONUCLEOTIDE DERIVATIVES

[75] Inventors: Kenichi Miyoshi; Toru Fuwa, both of Hiroshima, Japan

[73] Assignee: Wakunaga Seiyaku Kabushiki Kaisha, Osaka, Japan

[21] Appl. No.: 790,658

[22] Filed: Oct. 24, 1985

Related U.S. Application Data

[63] Continuation of Ser. No. 519,708, Aug. 2, 1983, abandoned.

[30] Foreign Application Priority Data

Aug. 9, 1982 [JP]   Japan .................. 57-138136

[51] Int. Cl.[4] .................................... C07H 21/04
[52] U.S. Cl. ............................ 536/27; 536/28; 536/29
[58] Field of Search .......................... 536/27, 28, 29

[56] References Cited

U.S. PATENT DOCUMENTS

| | | | |
|---|---|---|---|
| 3,873,521 | 3/1975 | Ekstrom et al. | 260/239.1 |
| 4,024,249 | 5/1977 | Muller et al. | 260/243 C |
| 4,401,796 | 8/1983 | Itakura | 525/340 |

FOREIGN PATENT DOCUMENTS 0106696  7/1982  Japan .

OTHER PUBLICATIONS

Nucleic Acids, Nucleotides, and Derivatives, 64 Nucleic Acids Research, Symposium Series No. 10, 1981, Miyoshi et al., Chemical Synthesis of 27-Desamidosecretin Gene by the Polymer Support Method.
Biochemistry, Chapter 22, Biosynthesis of Nucleotides and Chapter 24, DNA: Genetic Role, Structure and Replication.
Tetrahedron Letter, 1979, 38, pp. 3635–3638, Miyoshi et al., Solid Phase Synthesis of Nonadecathymidylic Acid by the Phosphotriester Approach.
Nucleic Acids Research, 8, 5491 (1980), Miyoshi et al., Solid-Phase Synthesis of Polynucleotides., III Synthesis of Polynucleotides with Defined Sequences by the Block Coupling Phosphotriester Method.
Nucleic Acids Research, 8, 5473 (1980), Miyoshi et al., Solid-Phase Synthesis of Polynucleotides., II., Synthesis of Polythymidylic Acids by the Block Coupling Phosphotriester Method.
Nucleid Acids Research, 8, 5507 (1980), Miyoshi et al., Solid-Phase Synthesis of Polynucleotides., IV., Usage of Polystyrene Resins for the Synthesis of Polydeoxyribonucleotides by the Phosphotriester Method.
Lee et al., 8-(6-Aminohexyl)-Amino-Adenine Nucleotide Derivatives for Affinity Chromatography, Arch. Biochem. Biophys. 163, 561 (1974).
Ishiwata et al., A New Affinity Adsorbent for Guanyloribonuclease, J. Biochem. 83, 783 (1978).
Ogilvie et al., The Chemical Synthesis of Oligoribonucleotides, IX., A Comparison of Protecting Groups in the Dichloridite Procedure, Can. J. Chem. 58, 2686–93 (1980).
Reese, The Chemical Synthesis of Oligo- and Poly-Nucleotides by the Phosphotriester Approach, Tetrahedron 34, 3143 at 3155 and 3160 (1978).

(List continued on next page.)

Primary Examiner—Johnnie R. Brown
Attorney, Agent, or Firm—Oblon, Fisher, Spivak, McClelland & Maier

[57] ABSTRACT

An oligonucleotide derivative having an amino group protected with an eliminatable group bonded through a phosphate group and a spacer with an appropriate length to the 5′-end of an oligonucleotide protected suitably at the 3′-hydroxyl group and the base moiety of the nucleotide, and an immobilized oligonucleotide derivative having a Sepharose carrier bonded to the amino group in place of said protective group are disclosed. Methods for production of these derivatives are also disclosed.

3 Claims, 30 Drawing Figures

OTHER PUBLICATIONS

Amarnath et al., Chemical Synthesis of Oligonucleotides, Chemical Reviews 77 (2), 183 at 188-195 (1977).

Watkins et al., Synthesis of Oligodeoxyribonucleotides Using N-Benzyloxycarbonyl-Blocked Nucleosides, J. Am. Chem. Soc. 104 (21), 5702-5708 (1982).

Gaffney et al., A New Strategy for the Protection of Deoxyguanosine During Oligonucleotide Synthesis, Tetrahedron Letters 23(22), 2257-60 (1982).

Kössel et al., Recent Advances in Polynucleotide Synthesis, Fortschr. Chem. Org. Natur. 32, 297 at 346-352 (1975).

Danenberg et al., Purification of Thymidylate Synthetase with 2'-Deoxyuridylate-Agarose, Chem. Abstracts 83:3354t (1974).

Smrt, Oligonucleotidic Compounds., LXIV., Synthesis of 6-Aminohexyl Esters of Uridine Nucleotides, Chem. Abstracts 91:5432f (1979).

Danilyuk et al., Positively Charged Analogs of Oligonucleotides, Synthesis of Aminohexyl Triester Derivatives of Oligothymidylates . . . ; Chem. Abs. 95:133293f (1981).

FIG. I

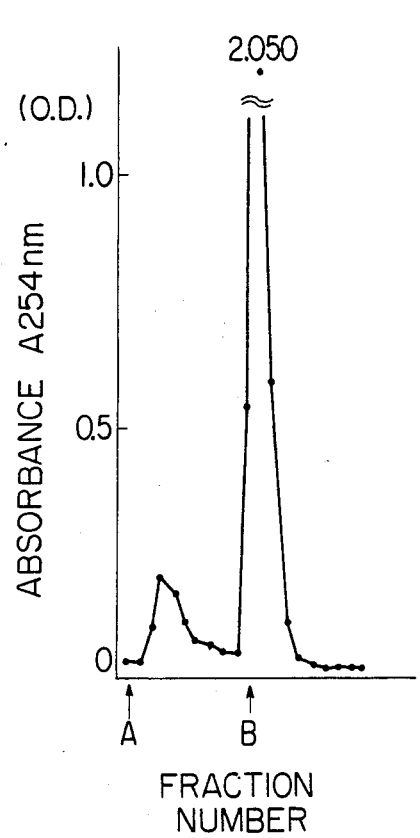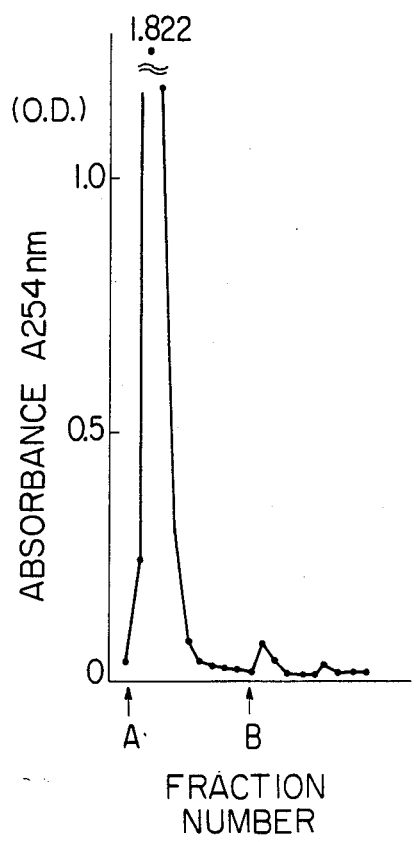

OLIGONUCLEOTIDE DERIVATIVES

This application is a continuation of application Ser. No. 519,708, filed Aug. 2, 1983, now abandoned.

BACKGROUND OF THE INVENTION

1. Field of the Art n relates to oligonucleotide derivatives having amino groups introduced through intermediary straight or branched alkylene groups into the 5'-phosphate groups of oligonucleotide of a certain length, to an immobilized oligonucleotide bound to a carrier at the amino group moiety, and to a method for production of them.

In the field of biochemistry, purification of vital polymers is one of the important tasks of research, and a great deal of effort by a large number of researchers have been made in the past therefor. For this object, affinity chromatography techniques and electrophoresis using primarily polyacrylamide gel have been developed and appreciably utilized.

Many vital polymers have inherent properties to bind or interact specifically with specific substances. Affinity chromatography may be said to be a method utilizing skillfully the principle of biological discrimination possessed by vital polymers.

Today, when the affinity technique is undergoing rapid progress, it is being widely utilized for purification and separation of various vital substances, including, as a matter of course, proteins, enzymes, and also lipids, hormones, vitamins, and receptors.

Above all, affinity chromatography with the use of a nucleic acid as ligand is expected to be widely utilized in the future in various applications, including isolation of nucleic acids or proteins which are also important in molecular biology. Also, for the purpose of efficient isolation, it is of great interest to develop a crosslinking method between ligands and carriers.

2. Prior Art

From such a point of view, among the affinity chromatographies using carriers having nucleic acids bound thereto, the most widely utilized is the method in which RNA containing poly (A) at the 3'-end is isolated by the use of an oligo (dT)-cellulose or a poly (U)-agarose column [Ono, M., Kondo, T., Kawakami, M : J. Biochem., 81, 941 (1977)].

Poly (U), Poly (dA)-cellulose, etc. are used in the method wherein the base moiety of nucleotide is bound to a carrier activated with BrCN, etc., and therefore the resultant bound product is stable due to binding formed at multiple sites therebetween, while, on the other hand, it involves a drawback in that its adsorption capacity is weakened, because the base moieties necessary for affinity activity are used for binding with the carrier [Lindberg, U., Persson, T. : Eur. J. Biochem., 31, 246 (1972)].

Also, in the case of oligo (dT)-cellulose, binding between the hydroxyl groups of a carrier and the phosphoric acid groups of an oligonucleotide is said to be accomplished by the use of, for example, DCC (dicyclohexylcarbodiimide), but it involves the problems of non-specific adsorption and lack of reproducibility of adsorption capacity.

Other than the proposals of immobilized homopolymers of nucleotide as described above, there are several proposals in which DNA obtained from natural resources is immobilized [Anderson, J. N., Monahan J. J., O'Malley, B. W.: J. Biol. Chem., 252, 5789 (1977)], but there has, insofar as we are aware, been no report in the past that an oligonucleotide of a certain length having any desired base sequence has been bound to a carrier only at a specific position to be successfully immobilized.

Under these circumstances, if an oligonucleotide having any desired base sequence could be bound to a carrier at a specific site, such a technique would be useful not only for isolation and purification of a mRNA according to affinity chromatography utilizing the immobilized nucleotide homopolymer but also for isolation and purification of a mRNA having a specific base sequence. Further, its applicability for purificarion of various nucleic acid related enzymes recognizing specific base sequences may also be considered.

A large number of researches have also been carried out on affinity carriers by using mono- or di-nucleotides as ligand, and the results of some of them are now commercially available. However, the sites at which the nucleotide is bound to the carrier through an intermediary spacer are mostly the base moieties thereof[a]. There are also some products in which the nucleotide is bound to the sites other than base moieties[b], but to the best of the present inventors' knowledge, such products involve the drawbacks of a large number of steps required for synthesis of the starting ligand and cumbersome procedures over the entire synthesis. Also, none of the methods can be used for oligonucleotide.

(a) Lee, C. Y., Lappi, D. A., Wermuth, B., Everse, J., Kaplan, N. O.: Arch. Biochem. Biophs., 168, 561 (1974); Ishiwata, K., Yoshida, H. : J. Biochem., 83, 783 (1978); Japanese Patent Laid-Open Nos. 25795/1977, 101396/1978, 133283/1978 and 36277/1980.

(b) Jervis, L., Pettit, N. M.: J. Chromatog., 97, 33 (1974); Lamed, R., Levin, Y., Wilchek, M. : Biochem. Biophys. Acta., 304, 231 (1973); Janski, A., Oleson, A. E. : Anal. Biochem., 71, 471 (1976).

SUMMARY OF THE INVENTION

Gist

In view of the state of the art as described above, the present inventors have developed an immobilized oligonucleotide which is useful in purification of nucleic acids and is utilizable for affinity resins, and a of producing the same.

The present inventors have previously developed a method of synthesizing a completely protected oligonucleotide according to the solid-phase synthetic method. The present inventors have found a method for immobilization, which comprises introducing a functional group capable of being bound with another carrier into the 5'-hydroxyl group of the objective compound synthesized by the solid-phase synthetic method, so as to be bound at said functional group to the carrier. According to this method, the present inventors have succeeded in synthesizing effectively an immobilized oligonucleotide, in which an oligonucleotide having any desired base sequence is bound at a specific position to a carrier.

The present invention concerns immobilized oligonucleotide derivatives, which can be used also as affinity resins as well as a plural number of oligonucleotide derivatives which can be used as intermediates thereof, and a method for production thereof.

More specifically, the oligonucleotide derivatives according to the present invention can be represented by the following formulae (2), (4) and (5).

The method of producing the oligonucleotide derivatives represented by the following formulae (2), (4) and (5), as expressed conceptionally and comprehensively, comprises causing a compound (1) to react with a compound (0) to produce a compound (2), while, on the other hand, condensing a compound (3′) obtained by the nucleic acid synthetic method with a compound (2′) which is a derivative of the compound (2) from which the protective group R⁴ of the 3′-phosphate has been eliminated to produce a compound (4), and removing all the protective groups from this compound to produce a compound (5).

$$HO(\underline{N}'_{px})_{\overline{m}}R^3 \quad (0)$$

$$R^2-NH-R^1-OH \quad (1)$$

$$R^2-NH-R^1-_{px}(\underline{N}'_{px})_{\overline{m}}R^3 \quad (2)$$

$$R^2-NH-R^1-_{px}(\underline{N}'_{px})_{m}H \quad (2')$$

$$HO(\underline{N}'_{px})_{n}\underline{N}'OCOR^4 \quad (3')$$

$$R^2-NH-R^1-_{px}(\underline{N}'_{px})_{m+n}\underline{N}'OCOR^4 \quad (4)$$

$$NH_2-R^1-_{p}(\underline{N}_{p})_{m+n}\underline{N}OH \quad (5)$$

In the above formulae, the respective symbols have the meanings set forth below:

$\underline{N}'$: a nucleoside having a base residue selected from the group consisting of adenine, guanine, cytosine and thymine, acylated to a necessary extent [acyl groups may be, for example, those from lower aliphatic mono-carboxylic acids ($C_2$–$C_4$) such as acetyl, isobutyryl, or those from aromatic carboxylic acids such as benzoyl, anisoyl], from which 3′- and 5′-oxygens in the riboside skeleton have been removed, that is A, G, C and T, respectively, namely:

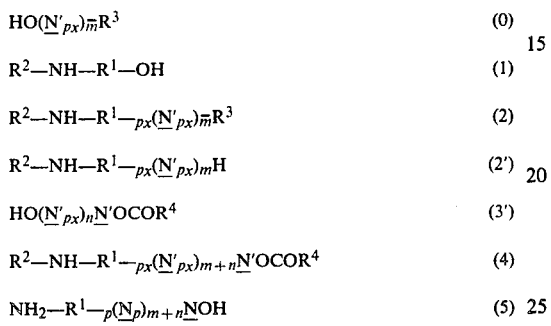

wherein B′ represents a base residue as mentioned above acylated to a necessary extent, provided that the plural number of N′ may be the same or different with respect to the base moiety and/or the acyl moiety when m or m+n (as described hereinafter) is 2 or more; the term "to a necessary extent" means a necessary extent required in nucleic acid synthesis, and therefore no acylation is necessary when the base is thymine; specific examples of acyl groups are benzoyl for adenine and cytosine and isobutyryl for guanine.

$\underline{N}$: a nucleoside having the above base residue not protected, from which the 3′- and 5′-oxygens in the riboside skelton have been removed; provided that plural number of N when m+n (as described hereinafter) is 2 or more may be the same or different.

$p_x$: phospho-triester bond, namely:

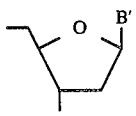

R°: a phenyl group or a substituted phenyl group such as o-chlorophenyl group or p-chlorophenyl group.

p: phospho diester bond, namely:

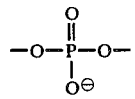

$R^1$: a straight or branched divalent hydrocarbon group, e.g., $C_2$–$C_{20}$ straight or branched alkylene group.

$R^2$: a protecting group for amino group which is substitutent stable during elimination of $R^3$ group and eliminatable while permitting the oligonucleotide moiety to remain stable, e.g., trifluoroacetyl group (Tfa-) or o-nitrophenylsulphenyl group (Nps-).

$R^3$: a protecting group for phosphate group which is substituent easily eliminatable under the conditions where all other protective groups are stable and capable of forming the terminal phosphoric acid triester bonding into a free phosphoric acid diester bonding, e.g., cyanoethyl group (CE), trichloroethyl group, phosphoroamidate group, etc.

$COR^4$: a protecting group for 3′-hydroxyl group conventionally used for oligonucleotide synthesis; $R^4$ being, for example, a lower (about $C_1$–$C_3$) alkyl group (e.g., methyl) or a lower alkyl- or lower alkoxy (about $C_1$–$C_3$)-substituted or non-substituted phenyl group (e.g., phenyl or methoxyphenyl) accordingly acetyl, benzoyl or anisoyl as $COR_4$, in the nucleotide liquid-phase synthesis, or a carrier for nucleotide synthesis with intermediary spacer, such as polystyrene derivatives, silica gel derivatives or polyacrylamide derivatives, in the nucleotide solid-phase synthesis.

$R^5$: a protecting group for 5′-hydroxyl group conventionally used for oligonucleotide synthesis, for example, substituted (e.g., dimethoxy-substituted) or unsubstituted (trityl group).

m: an integer 0 to 6 (preferably 1 to 4)

n: an integer 0 to 40 (preferably 0 to 20).

In the above formulae, among p or $p_x$ or HO or O, those positioned at the right side of $\underline{N}'$ or $\underline{N}$ or the bracket including these represent those bonded to the 3′-hydroxyl group of the nucleoside, while those on the left side thereof represent those bonded to the 5′-hydroxyl group of the nucleoside.

The immobilized oligonucleotide according to the present invention is represented by the following formula (6).

The method of producing an immobilized oligonucleotide represented by the following formula (6) according to the present invention comprises causing a compound (5) to react with a Sepharose derivative capable of being bound with an amino group at the amino group of the oligonucleotide derivative to produce a compound (6).

$$NH_2-R^1-_{p}(\underline{N}_{p})_{m+n}\underline{N}OH \quad (5)$$

$$[Sepharose]-NH-R^1-_{p}(\underline{N}_{p})_{m+n}\underline{N}OH \quad (6)$$

wherein the respective symbols have the following meaings: $\underline{N}$, $\underline{N}'$, px, p, $R^1$, $R^2$, $R^3$, $R^4$, $R^5$, m and n are the same as those defined above; [Sepharose] is a residue of Sepharose derivative capable of being bound with an amino group.

To represent more specifically the various formulae as symbolized above to be used in the present invention, the formula (4), for example, can be represented as follows:

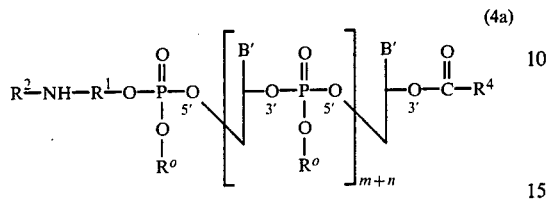

(4a)

In the present invention, to speak of the compound (4), the representation by the formula (4) may be used interchangeably with that of the formula (4a).

Advantageous Effect

According to the present invention, it is possible to synthesize an immobilized oligonucleotide useful also as an affinity resin, comprising an oligonucleotide with a certain length and having any desired base sequence bonded at a specific site to a carrier, and the bonding unattainable by the method of the prior art can be attained to produce a resin of improved quality by the method of the present invention.

This is because a primary amino group has been introduced in an oligonucleotide as a functional group for binding the oligonucleotide with the carrier. That is, the following meritorious effects can be considered to be realized by the functional group.

(1) The functional group has higher reactivity with other functional groups (hydroxyl groups, phosphoric acid groups and amino groups at the base moieties).

(2) Therefore, even when a mixture of deprotected oligonucleotides is used without purification for condensation with the carrier, selective binding at this position is possible by employment of suitable reaction and other conditions.

Also, as the result, it has become possible to immobilize by a simple step and moreover effectively an oligonucleotide having any desired base sequence which has been synthesized according to any of the solid-phase methods and the liquid-phase methods.

Further, by avoiding binding at the base moiety which interferes with the adsorption activity, the immobilized oligonucleotide obtained by the present invention has excellent adsorption capacity.

Accordingly, the oligonucleotide-Sepharose according to this invention is superior by far in adsorption capacity, reproducibility, selectivity, and durability to those of the prior art [oligo (dT)-cellulose and poly (U)-agarose].

BRIEF DESCRIPTION OF THE DRAWINGS

In the accompanying drawings:

FIGS. 10, 11, 12, 13, 15, 19 and 20 are graphs respectively showing column chromatograms by affinity carriers.

Figure 1:
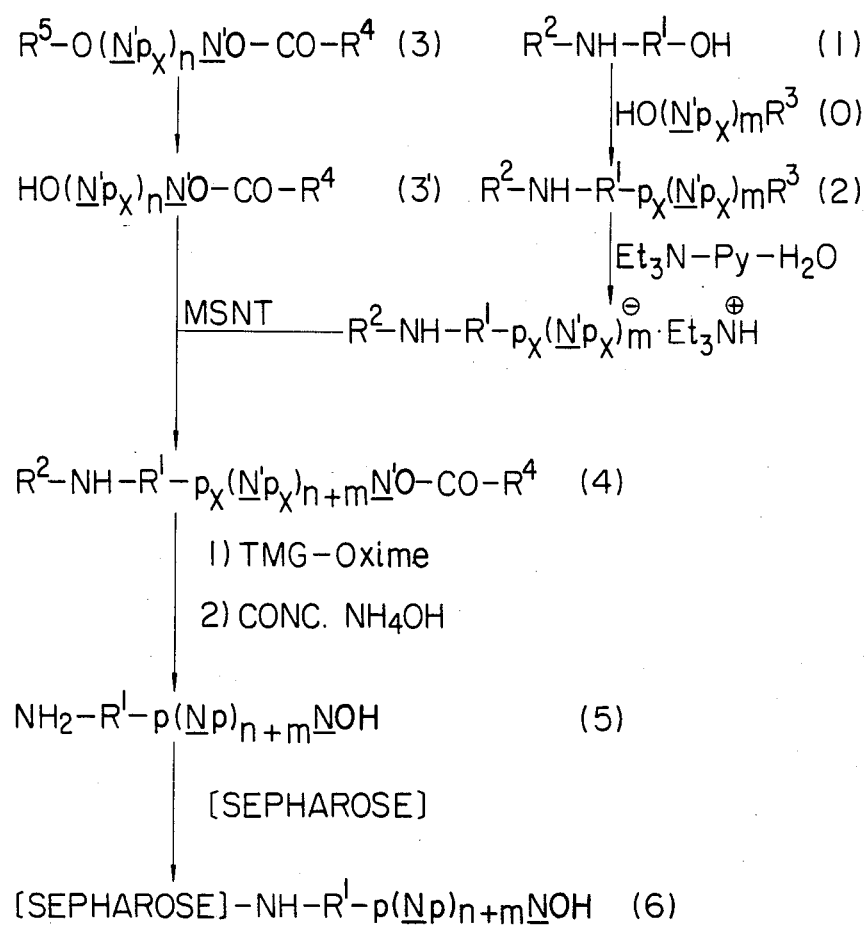
FIG. 1 is a scheme showing a series of reactions to which the present invention is related.

(a) Purification conditions by Sephadex G-50 column:
Column: Sephadex G-50
Column volume: 1.5 cm × 120 cm
Eluant: 50 mM TEAB buffer, pH 7.5
Fraction amount: 35 droplets/fraction (b) Analytical conditions by HPLC:
Column: μ-Bondapak C18 (Waters)
Eluant: $CH_3CN$ in 0.02 M EDAA buffer (pH 7.8)
Gradient: as shown in the drawings
Flow rate: 2 ml/min.
Chart speed: 10 mm/min.
Temperature: 50° C.

(c) Assay conditions by affinity chromatography column:
Washing solution: 0.5 M NaCl, 10 mM Tris-HCl
Eluant: 10 mM Tris-HCl (pH 7.5)
Fraction amount: 15 droplets (350 μl)
Application of vital test sample is indicated by A and initiation of elution by B.

DETAILED DESCRIPTION OF THE INVENTION

Reaction Scheme

The present invention can be comprehended as a link in the production of an immobilized oligonucleotide, having an oligonucleotide with a base sequence capable of synthesis bound to a carrier, and the reaction starting from the oligonucleotide synthesized by the solid phase method along its best mode from this point may be illustrated as in FIG. 1.

The symbols in this reaction scheme have the following meanings.

MSNT: mesitylenesulfonyl nitrotriazolide
TMG-Oxime: 0.5 M tetramethylguanidium pyridine-2-aldoxime in dioxane/water (9:1)

In the following description, specific compounds (1) to (6) are to be explained in this order on the basis of this reaction scheme.

Concerning chemical synthesis of nucleotides or nucleic acids, a number of textbooks and reviews have already been published. Accordingly, for details, other than those in the following description, relating to the kinds of protecting groups, their introduction or removal as well as condensation and other features in the synthesis of deoxyoligoribonucleoside according to the present invention, reference is made to, for example, H. Kössel, H. Seliger: PROGRESS IN THE CHEMISTRY OF ORGANIC NATURAL PRODUCTS, Vol. 32, p.297, Springer, Wien (1975) and Tetrahedron, Vol. 34, 3143 (1978).

Compound (1)

The compound (1) is represented by the formula (1):

$$R^2—NH—R^1—OH \tag{1}$$

The compound (1) can be obtained by introduction of $R^2$ as a protecting group for the amino group of ω-amino alcohol ($NH_2—R^1—OH$).

$R^1$ is a straight or branched divalent hydrocarbon, suitably a $C_2-C_{20}$, preferably $C_2-C_{12}$, alkylene group. As ω-amino alcohols, those of $C_2-C_{12}$ are commercially available.

$R^2$ is a protecting group, which is stable under the eliminating conditions of $R^3$ group (—CE) (e.g., in $Et_3N$-pyridine-$H_2O$ 1:3:1) or phosphorylating conditions, [e.g., in pyridine-1-methylimidazole, or in DMAP (dimethylaminopyridine) in pyridine (hereinafter referred to as Py in some cases)], and is further capable of being eliminated while the oligonucleotide moiety remains stable.

If possible, it is more convenient that the protecting group $R^2$ be one which can be eliminated at the same time under such conditions for removing the protecting groups of the oligonucleotide as in, for example, conc. ammonia water.

Specific examples of the protecting group of the amino group are trifluoroacetyl group which can be removed by conc. ammonia water and o-nitrophenylsulphenyl group which can be removed by a weak acid or mercaptoethanol.

Compound (2)

(1) Definition:
The compound (2) is a novel substance represented by the formula (2):

The definitions of the substituents in the compound (2) and preferable examples are as set forth above.

(2) Synthesis:
The compound (2) can be prepared by bonding the 5'-hydroxyl group of the oligonucleotide derivative represented by the following formula (0) to the compound of the above formula (1) through a phosphate group. This bonding can be obtained by phosphorylating the 5'-hydroxyl group of the compound (0) with a bivalent phosphorylating agent (e.g., phospho-ditriazolide, phospho-dichloride or phospho-bibenzotriazolide) and then carrying out the reaction with the compound (1) under condensing conditions (preferably in the presence of 1-methyl-imidazole). Specific examples of the reaction conditions are set forth in the experimental examples presented below.

Compound (3)

The compound (3) is represented by the formula (3):

The compound (3) is an oligonucleotide completely protected in a broad sense, and it may be synthesized according to any method.

The oligonucleotide of the compound (3) is protected at its 3'-end by $R^4$ through the carbonyl group. That is, this hydroxyl group is acylated. Definition of $R^4$ and examples thereof are as given above. When the compound (3) is synthesized according to the solid-phase method (to be described in detail hereinafter), $COR^4$ is suitably a carrier having an appropriate spacer (e.g., polystyrene derivative, polyacrylamide derivative, etc.). As to a polystyrene resin as $COR^4$, see Chem. Rev. 77, 183 (1977); and Forsuchr. Chem. Org. Naturstoff, 32, 297 (1975); as to a polyamide resin, see J. Am. Chem. Soc., 98, 8514 (1976); Nucleic Acids Research 4, 1135 (1977); ibid. 4, 4391 (1977); ibid. 6, 1265 (1979); and Tetrahedron Letters, 1979, 1819.

The compound (3) can be synthesized according to any method suited for the purpose. Generally speaking, as synthesizing methods for an oligonucleotide such as the compound (3), there are the triester method, the phosphite method and respective solid-phase and liquid-phase methods, but it is preferable to use the solid-phase method developed by the present inventors. Details of the solid-phase synthesizing method are described in Tetrahedron Letters 1979, 3635 (1979); Nucleic Acids Research 8, 5473 (1980); ibid. 8, 5491 (1980); ibid. 8, 5507 (1980); and Nucleic Acids Research Symposium Series 7, 281 (1980).

Compound (3')

The compound (3') corresponds to the compound (3) from which the protective group $R^5$ at the 5'-end has been removed.

For removing only the 5'-protecting group of the compound (3), when $R^5$ is a group conventionally used, the method in which the compound (3) is treated in a 1.0 M isopropanol-methylene chloride solution of benzenesulfonic acid, acetic acid or zinc bromide, or some other method may be used.

Compound (4)

(1) Definition:
The compound (4) is a novel substance represented by the formula (4):

The definitions of the substituents in the compound (4) and preferable examples are as described above.

(2) Synthesis:
The compound (4) can be obtained by eliminating the $R^3$ group in the compound (2) and the $R^5$ group in the compound (3), respectively and then causing the reaction of the both compounds between the 3'-phosphate group on the compound (2) and the 5'-hydroxyl group on the compound (3) in the presence of a condensing agent.

The $R^3$ group of the starting compound (2) is an easily eliminatable group, and the 3'-phosphate of the oligonucleotide after deprotection may be $PO\ominus$ (free form) or in the form of a suitable salt. As the $R^3$ group, a cyanoethyl group is generally used, and typical examples of salts are tertiary amine salts, for example, triethylammonium salt.

The other starting compound corresponding to the compound (3) from which $R^5$ has been removed, namely, the compound (3'), is as described above.

Condensation is conducted preferably in the presence of a condensing agent. Typical examples of condensing agents which can be used in this step are tosyl chloride, mesitylene sulfonyl chloride, mesitylene sulfonyl tetrazolide (MSTe) and mesitylene sulfonyl nitrotriazolide (MSTN). As for specific examples of the reaction conditions, see the Experimental Examples set forth below.

Compound (5)

(1) Definition:
The compound (5) is a novel substance represented by the formula (5):

The definition of the substituent in the compound (5) and preferable examples are as given above.

(2) Synthesis:
The compound (5) can be prepared by eliminating the $COR^4$ group, the $R^2$ group, the acyl group on the base and the protective groups (usually aryl groups, for example, o-chlorophenyl group) in the phospho triester in the compound (4) while the oligonucleotide remains stable.

The COR⁴ group and o-chlorophenyl group in phospho triester is preferably eliminated by the use of a TMG-Oxime solution. Other protecting groups ($R^2$ group and acyl group at the base moiety) may also be removed by carrying out an alkali treatment (conc. ammonia water). The TMG-Oxime solution refers to 0.5 M tetramethylguanidium pyridine-2-aldoxamate in dioxane/water (9:1).

When $R^2$ is Tfa-, it can be eliminated by ammonia treatment, but when it is Nps-, further treatment with mercaptoethanol is necessary. When other protective groups are employed, still another treatment may also be considered, provided that the oligonucleotide moiety remains stable.

As for the specific examples of the reaction conditions, see the Experimental Examples set forth below.

Compound (6)

(1) Definition:
The compound (6) is a novel substance represented by the formula (6):

$$[\text{Sepharose}]-\text{NH}-R^1{}_{-p}(\underline{N}_p)_{m+n}\underline{N}\text{OH} \quad (6)$$

The definition of the substituent in the compound (6) and preferable examples thereof are as mentioned above.

(2) Synthesis:
The compound (6) can be prepared by condensation of the compound (5) with a Sepharose derivative capable of binding with amino group. A condensing agent may be necessary or unnecessary depending on the kind of the Sepharose derivative to be bonded.

Sepharose as its chemical entity is agarose and is available from Pharmacia Fine Chemicals, U.S.A. This material, in spite of its chemical entity being agarose, is conventionally called "Sepharose" and is well known to those skilled in the art. For example, see "Affinity Chromatography", Elsevier Scientific Pub. Co., Amsterdam (1978); Agric. Biol. Chem. 80, 409 (1976). Some examples of Sepharose derivatives which can be used in the present invention are enumerated below.

Cyanogen bromide activated Sepharose:

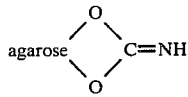

Activated CH Sepharose:

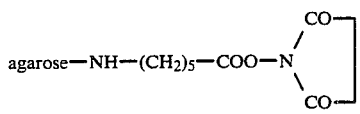

Epoxidized Sepharose:

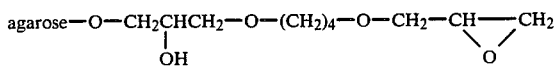

CH Sepharose:

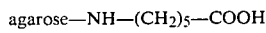

AH Sepharose:

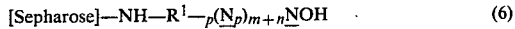

Among these derivatives, the first three, especially the first two, are preferred from the standpoint that no condensing agent (e.g., DCC) is required for their use.

The reaction between the compound (5) and the Sepharose derivative can be carried out according to any suitable method which enables the reaction of the primary amino group extending from the 5'-end with a group in the Sepharose derivative capable of reacting with that amino group (e.g., carboxyl group) such as formation of amide bonding through dehydration. Such a method is basically known in the art. Details of this method are set forth in the Experimental Examples presented hereinafter.

When there is a possibility of a reaction occurring at groups other than the desired primary amino group extending from the 5'-end depending on the kind of the Sepharose derivative employed and/or the condensing conditions, the other groups of the compound (5) may be protected. Accordingly, the expression "causing an oligonucleotide to react with a Sepharose derivative capable of binding with amino group at the amino group of the oligonucleotide derivative" used in the present invention is also inclusive of a case wherein the compound (5) is protected in such a manner, and this expression is also inclusive of a case wherein the Sepharose derivative is in the form of its functional derivative.

(3) Assay of binding amount and adsorption capacity:
The amount of the compound (5) and Sepharose bound is shown by the amount of the compound (5) bound per 1 mg of Sepharose or the amount adsorbed when using $HOA_{13}$ or $HOT_{13}$ as a material to be adsorbed, which is expressed in terms of OD unit.

Also, for comparison between the compound (6) synthesized according to the present invention and the carrier synthesized according to the method of the prior art [oligo(dT)-cellulose or oligo(dA)-cellulose (both of which are commercial products)], similar adsorption tests were conducted.

Similarly, as confirmation of formation of the compound (6) (namely determination of the binding amount), examination of bonding of the oligonucleotide having no amino group extending from the 5'-phosphate group according to the present invention such as tridecaadenylic acid($HOA_{13}$), tridecathymidylic acid ($HOT_{13}$) is important for establishing the bond positions.

As a result, it is possible to obtain a compound (6) which exhibits a binding amount approximating a level of 0.06 OD/mg, and it can be seen that all of the compounds (5) can be bonded irrespective of their base sequences. Also, because there occurs no bonding between an oligonucleotide having no amino group and a carrier whatsoever, it can be seen that the compound (5) undergoes no bonding at its base moiety but only through its primary amino group.

On the other hand, according to the experiments by the present inventors, among the commercially available resins, an adsorption capacity of about 0.010 to 0.037 OD/mg was sometimes assayed in oligo(dT)-cellulose, but no reproducible value was obtained when the same assay was repeated again. On the other hand, there exists substantially no adsorption capacity in oligo(dA)- cellulose [which may explain the fact known in the art that there is no oligo(dA)-cellulose of good quality, as compared with oligo(dT)-cellulose].

Thus, the compound (6) of the present invention may be said to be an affinity carrier of improved quality, which is bound to a carrier only through the primary amino group existing at the tip of the spacer newly developed, entirely free from non-specific bonding at other portions (e.g., amino group on the base moiety) and enables bonding of an oligonucleotide having any synthesizable base sequence to a carrier.

EXPERIMENTAL EXAMPLES

A. Compound (1) [Synthesis of $R^2$—NH—$R^1$—OH]

Example 1 - 1 [the case where $R^1$ = Hex (i.e., $C_6H_{12}$—), $R^2$ = Tfa]

(1) Reagent:
6-Aminohexanol (1.17 g, 10 mmol)
Trifluoroacetyl thioethyl (Tfa-SEt) (1.80 ml, 14.4 mmol)
Dioxane (15 ml)

(2) Synthesis:

6-Aminohexanol (in an amount as shown above) was dissolved in dioxane (15 ml), and trifluoroacetyl thioethyl (Tfa-SEt) (in an amount as shown above) was gradually added to the resultant solution, and the reaction was carried out at room temperature overnight. After the reaction, the mixture was concentrated and the residue dissolved in ether, after which extraction is carried out three times with water. The ether layer was dried over anhydrous sodium sulfate and concentrated. The residue was dissolved with addition of ether, and pentane was added for crystallization to produce the compound (1 - 1) as the powdery product.

Yield: 1.40 g (70%)

Example 1-2 [the case where $R^1$ = Et (i.e., —$CH_2CH_2$—), $R^2$ = Nps]

The procedure in Example 1—1 was carried out with the use of 2-aminoethanol ($NH_2$—EtOH) and o-nitrophenylsulphenylchloride (Nps—Cl).

Example 1-3 [the case where $R^1$ = Hex, $R^2$ = Nps]

The procedure in Example 1—1 was carried out with the use of 2-aminohexanol ($NH_2$—HexOH) and o-nitrophenylsulphenyl chloride (Nps—Cl).

TABLE 1

| Example | Product | | Yield |
|---|---|---|---|
| 1-1 | $R^1$ = Hex, | $R^2$ = Tfa | 70% |
| 1-2 | $R^1$ = Et, | $R^2$ = Nps | 79% |
| 1-3 | $R^1$ = Hex, | $R^2$ = Nps | 72% |

B. Compound (2) [Synthesis of $R^2$—NH—$R^1_{px}(\overline{N'_{px}})_m R^3$]

Example 2 - 1 [the case where $R^1$ = Hex, $R^2$ = Tfa, $\underline{N'}$ = $A_{Bz}$, m = 2 and $R^3$ = CE]

(1) Reagent
HO $A^{Bz}_{px} A^{Bz}_{px}$ CE (Bz is $N^6$-benzoyl group) (800 mg, 0.71 mmol)
o-Chlorophenyl phosphoroditriazolide (1.0 mmol) in Dioxane (6.0 ml)
Compound (1 - 1) (300 mg, 1.4 mmol)
1-Methyl-imidazole (115 mg, 1.4 mmol)

(2) Synthesis:

To $HOA^{Bz}_{px}A^{Bz}_{px}$ CE (in an amount as shown above) made anhydrous by azeotropy with Py was added a solution of o-chlorophenyl phosphoroditriazolide (in an amount as shown above) in dioxane (in an amount as shown above), and the reaction was carried out for 2 hours. The progress of the reaction was checked by TLC ($CHCl_3$—MeOH=14:1), and the compound (1 - 1) (in an amount as shown above) and 1-methyl-imidazole (in the amount shown above) were then added to the mixture, and the reaction was carried out for 2 hours. The progress of the reaction was checked by TLC, and then water was added to decompose excessive triazolide. The solvent was evaporated off. The residue was dissolved in $CHCl_3$, washed with water, 0.5 M-$NaH_2PO_4$, saturated $NaHCO_3$ and 5% NaCl aqueous solution and thereafter dried over anhydrous sodium sulfate. The $CHCl_3$ layer was concentrated and purified through a silica gel short column (eluant : 0–4% MeOH/$CHCl_3$). The desired product was collected, concentrated, and the concentrate was added dropwise into pentane to obtain a powdery compound (2 - 1).

Yield: 610 mg (57%)

Examples 2—2 to 2- 6

The procedure in Example 2- 1 was carried out with the use of materials listed in Table 2 to obtain the results shown in Table 2 below.

TABLE 2

| Example | Product | Yield |
|---|---|---|
| 2-1 | $R^1$ = Hex, $R^2$ = Tfa, $\underline{N'}$ = $A^{Bz**}$, m = 2, $R^3$ = CE | 57% |
| 2-2 | $R^1$ = Hex, $R^2$ = Tfa, $\underline{N'}$ = $A^{Bz}$, m = 1, $R^3$ = CE | 86% |
| 2-3 | $R^1$ = Hex, $R^2$ = Tfa, $\underline{N'}$ = T, m = 2, $R^3$ = CE | 72% |
| 2-4 | $R^1$ = Hex, $R^2$ = Tfa, $\underline{N'}$ = T, m = 1, $R^3$ = CE | 95% |
| 2-5 | $R^1$ = Hex, $R^2$ = Nps, $\underline{N'}$ = T, m = 2, $R^3$ = CE | 46% |
| 2-6 | $R^1$ = Pen*, $R^2$ = Tfa, $\underline{N'}$ = $G^{iBu}$, m = 2, $R^3$ = CE | 51% |

*Pen = —$C_5H_{10}$—
**A, T and G mean the groups $\underline{N}$ derived from nucleoside, when the base is adenine, thymine and guanine, respectively; Bz indicates benzoyl and iBu isobutyryl.

C. Compound (3) [Synthesis of $R^5$—O($N'_{px}$)$_n N'OCOR^4$]

Example 3 - 1 (the case where $N'$ = $A^{Bz}$, n = 12, $R^5$ = DMTr, and $R^4$ = —⌇— (Ps) *)

(1) Reagent:
DMTr—OA$^{Bz}$OCO—⌇— (Ps) (300 mg, 0.033 mmol)
DMTr—OA$^{Bz}_{px}$A$^{Bz}_{px}\ominus Et_3N\oplus H$ (150 mg, 0.1 mmol)
MSNT (150 mg, 0.5 mmol)

*) DMTr is dimethoxytrityl, —⌇— (Ps) is —($CH_2$)$_2$CONHC-$H_2$—⌇— (Ps) ( Ps is polystyrene).

(2) Synthesis:

DMTr—OA$^{Bz}$OCO—⌇— (Ps) was sampled (in the amount shown above), (1) washed with iso-PrOH—$CH_2Cl_2$ (15:85 v/v, 10 ml×3), (2) detritylated with 0.1 M $ZnBr_2$ solution in isoPrOH—$CH_2Cl_2$ (15:85 v/v, 8 ml×4, total 20 minutes), (3) washed with iso-PrOH—$CH_2Cl_2$ (15:85 v/v, 10 ml×3), (4) washed with pyridine (Py.) (10 ml×3), and then (5) treated with Py—$Et_3N$—$H_2O$ (3:1:1 v/v, 10 ml, 30 minutes) to be made anhydrous, which step was followed by addition of a Py solution of DMTr—OA$^{Bz}_{px}$A$^{Bz}_{px}\ominus Et_3N\oplus H$ (in the amount shown above) for azetropy with Py, to be made completely anhydrous. (6) To the resultant mixture were added MSNT (in the amount shown above) and anhydrous Py (2 ml), and the reaction was carried out with shaking for 90 minutes. After (7) washing with Py (10 ml×3), (8) the reaction was carried out with addition of Ac$_2$O—Py (1:9 v/v, 10 ml) containing a catalytic amount of dimethylaminopyridine (DMAP) for 10 minutes to protect the unreacted 5'-hydroxyl groups. (9) By washing with Py (10 ml×3), the first condensation was completed.

This procedure was repeated similarly 6 times to obtain the desired compound (3 - 1) (tridecaadenic acid).

The yields by quantitative determination of trityl groups for respective reactions were found to be 89%, 83%, 80%, 79%, 81% and 90%, respectively.

Overall yield: 34%.

Example 3 - 1' (Deprotection)

Figure 2:
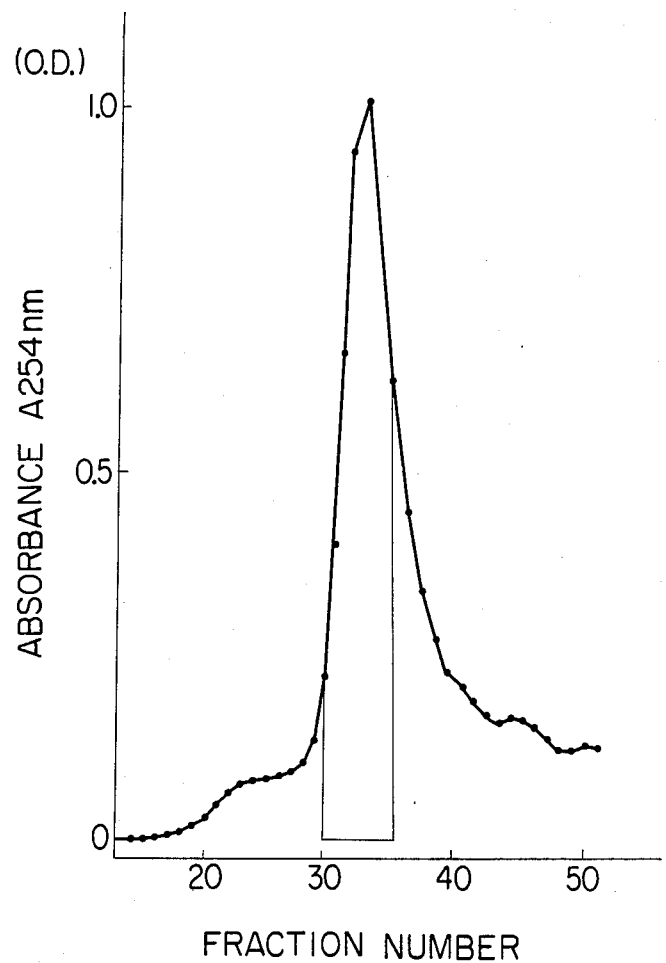
FIGS. 2, 4, 5 and 6 are graphs respectively showing Sephadex column chromatograms.

DMTr—O(A$^{Bz}_{px}$)$_{12}$A$^{Bz}$OCO—∿—Ps (15 mg) was sampled in a centrifugal precipitating tube, and a solution of 0.5 M TMG-Oxime in pyridine-H$_2$O (9:1 v/v) (100 μl) was added thereto, after which the mixture was left to stand at room temperature for 24 hours. To this mixture was added conc. ammonia (2.5 ml), and the resultant mixture was left to stand in sealed state at 50° C. overnight. The resin was filtered off, and the filtrate was concentrated, dissolved in water, and extracted three times with ether. The aqueous layer was concentrated and desalted with Sephadex G-50 (1.5×120 cm) [eluant: 0.05 M-TEAB (triethylammonium bicarbonate) buffer, pH 7.5]. The elution pattern as shown in FIG. 2.

Figure 3:
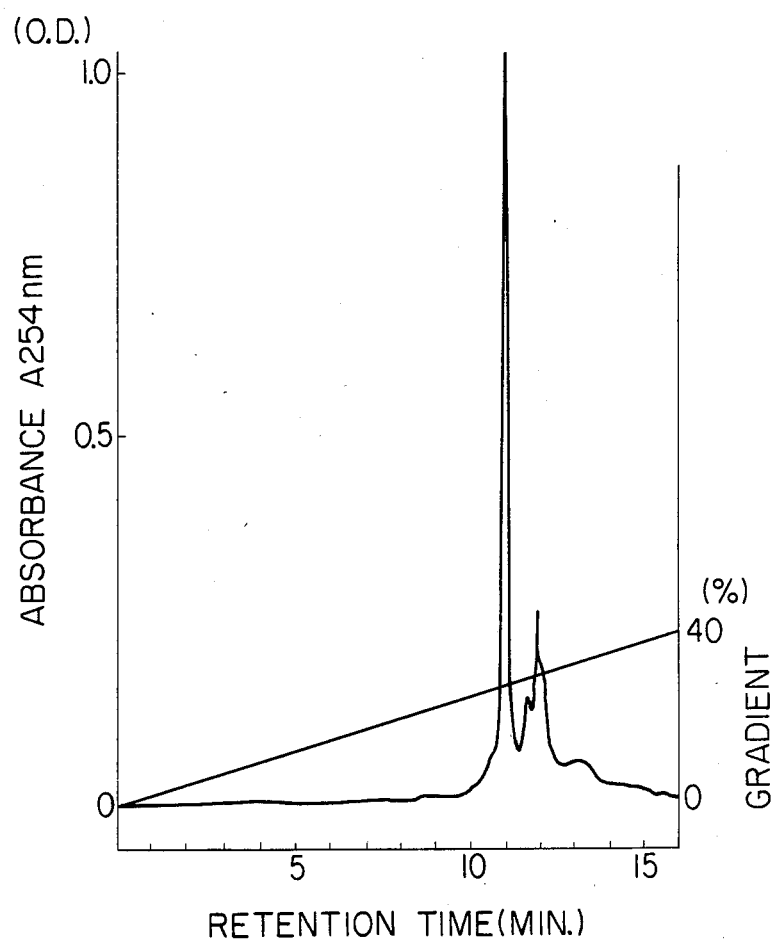
FIGS. 3, 7, 8, 9, 14, 16, 17 and 18 are graphs respectively showing HPLC patterns.

The portions of the peaks obtained were collected, concentrated and treated with 80% acetic acid (2 ml, 10 minutes) to obtain tridecaadenylic acid (HOA$_{13}$). The purity of this product was checked by HPLC (μ-Bondapak C-18), and the elution pattern obtained is shown in FIG. 3.

Examples 3 - 2' to 3 - 6'

As already reported, in the following papers, various compounds (3) were synthesized by repeating the procedure in Example 3 - 1. The yield obtained per condensation is about 85% on an average.

Tetrahedron Letters 1979, 3635 (1979)
Nucleic Acids Research 8, 5473 (1980)
Nucleic Acids Research 8, 5491 (1980)
Nucleic Acids Research 8, 5507 (1980)
Nucleic Acids Research Symposium Series 7, 281 (1980)
J. Am. Chem. Soc., 103, 706 (1981)
Nucleic Acids Research 10, 197 (1981)

D. Compound (4) [Synthesis of R$^2$—NH—R$^1$—O$_{px}$ (N'$_{px}$)$_{m+n}$N'OCOR$^4$]

Example 4 - 1 (R$^1$=Hex, R$^2$=Tfa, N=A$^{Bz}$, m=2, n=12, R$^4$=—∿—(Ps))

(1) Reagent:
Compound (3 - 1) (DMTr—O(A$^{Bz}_{px}$)$_{12}$A$^{Bz}$OCO—∿—(Ps)) (115 mg, 3.45 μmol)
Compound (2 - 1) [Tfa—NH—Hex$_{px}$(A$^{Bz}_{px}$)$_2$CE](60 mg, 0.4 mmol)
MSNT (60 mg, 0.2 mmol)

(2) Synthesis:
The compound (3 - 1) (DMTr—O(A$^{Bz}_{px}$)$_{12}$A$^{Bz}$OCO—∿—(Ps)) was sampled (in the amount shown above), swelled well with isoPrOH—CH$_2$Cl$_2$ (15:85 v/v, 10 ml×3) and then detritylated with a solution of 1 M—ZnBr$_2$ in isoPrOHCH—CH$_2$Cl$_2$ (15:85 v/v, 5 ml×6, 30 minutes). The resin was washed with isoPrOH—CH$_2$Cl$_2$ (15:85 v/v, 5 ml×3) and then with Py (5 ml×3). On the other hand, the compound (2 -1) [Tfa—NH—Nex—$_{px}$(A$^{Bz}_{px}$)$_2$CE] (in the amount shown above) was sampled and subjected to decyanoethylation by treatment with Py—Et$_3$N—H$_2$O (3:1:1, 3 ml, 15 minutes). After evaporation of the solvent, the residue was subjected twice to azeotropy with Py. This was then dissolved in Py, and the resultant solution was added to the previous resin, the mixture being azeotroped with Py to be made completely anhydrous. MSNT (in the amount shown above) and anhydrous Py (15 ml) were added to this mixture, and the reaction was carried out with shaking for 90 minutes. After the reaction, the resin was washed with Py and MeOH then dried to produce the compound (4 - 1).

Yield: 120 mg.

Example 4 - 2

Similarly as in Example 4 - 1, with the use of the compound (3 - 2) [DMTr—O(T$_{px}$)$_{12}$TOCO—∿—(Ps)] and the compound (2 - 3) [Tfa—NH—Hex—$_{px}$(T$_{px}$)$_2$CE], the compound (4 - 2) [Tfa—NH—Hex—$_{px}$ (T$_{px}$)$_{14}$TOCO—∿—(Ps)] was synthesized.

Example 4 - 3

Similarly as in Example 4 - 1, with the use of the compound (3 - 3) [DMTr—O(A$^{Bz}_{px}$)$_9$A$^{Bz}$OCO—∿—(Ps)] and the compound (2 - 1) [Tfa—NH—Hex—$_{px}$(A$^{Bz}_{px}$)$_2$CE], the compound (4 - 3) [Tfa—NH—Hex—$_{px}$ (A$^{Bz}_{px}$)$_{11}$A$^{Bz}$OCO—∿—(Ps)] was synthesized.

Example 4 - 4

Similarly as in Example 4 - 1, with the use of the compound (3 - 4) [DMTr—OG$^{iBu}_{px}$G$^{iBu}_{px}$G$^{iBu}_{px}$G$^{iBu}_{px}$A$^{Bz}_{px}$A$^{Bz}_{px}$G$^{iBu}_{px}$C$^{Bz}_{px}$T$_{px}$T$_{px}$C$^{Bz}_{px}$C$^{Bz}$OCO—∿—(Ps)]
and the compound (2 - 3) [Tfa—NH—Hex—$_{px}$ (T$_{px}$)$_2$CE], the compound (4 - 4) [Tfa—NH—Hex—$_{px}$ (T$_{px}$)$_2$G$^{iBu}_{px}$ GiBu$_{px}$ G$^{iBu}_{px}$A$^{Bz}_{px}$A$^{Bz}_{px}$G$^{iBu}_{px}$C$^{Bz}_{px}$T$_{px}$T$_{px}$C$^{Bz}_{px}$C$^{Bz}_{px}$C$^{Bz}$OCO—∿—(Ps)] was synthesized.

Example 4 - 5

Similarly as in Example 4 - 1, with the use of the compound (3 - 2) [DMTr—O(T$_{px}$)$_{12}$TOCO—∿—(Ps)] and the compound (2 - 5) [Nps—NH—Hex—$_{px}$(T$_{px}$)$_2$CE], the compound (4 - 5) [Nps—NH—Hex—$_{px}$ (T$_{px}$)$_{14}$TOCO—∿— ] was synthesized.

Example 4 - 6

Similarly as in Example 4 - 1, with the use of the compound (3 - 4) [DMTr—OG$^{iBu}_{px}$A$^{Bz}_{px}$A$^{Bz}_{px}$G$^{iBu}_{px}$C$^{Bz}_{px}$T$_{px}$T$_{px}$T$_{px}$C$^{Bz}_{px}$A$^{Bz}_{px}$C$^{Bz}_{px}$G$^{iBu}_{px}$T$_{px}$A$^{Bz}_{px}$A$^{Bz}$OCO—∿—(Ps)]
and the compound (2 - 6) [Tfa—NH—Pen—$_{px}$(G$^{iBu}_{px}$)$_2$CE], the compound (4 - 6) [Tfa—NH—Pen—$_{px}$ (G$^{iBu}_{px}$)$_2$G$^{iBu}_{px}$A$^{Bz}_{px}$A$^{Bz}_{px}$G$^{iBu}_{px}$C$^{Bz}_{px}$T$_{px}$T$_{px}$T$_{px}$C$^{Bz}_{px}$A$^{Bz}_{px}$C$^{Bz}_{px}$G$^{iBz}_{px}$T$_{px}$A$^{Bz}_{px}$A$^{Bz}$OCO—∿—(Ps)] was synthesized.

Example 4 - 7

Similarly as in Example 4 - 1, with the use of the compound (3 - 6) [DMTr—OG$^{iBu}_{px}$T$_{px}$C$^{Bz}_{px}$ G$^{iBu}_{px}$A$^{Bz}_{px}$C$^{Bz}_{px}$T$_{px}$A$^{Bz}_{px}$-A$^{Bz}_{px}$C$^{Bz}_{px}$G$^{iBu}_{px}$C$^{Bz}_{px}$A$^{Bz}_{px}$G$^{iBu}_{px}$ TOCO—〰— (Ps)] and the compound (2 - 6) [Tfa—NH—Pen—$_{px}$(G$^{iBu}_{px}$)$_2$CE], the compound (4 - 7) [Tfa—NH—Pen—$_{px}$(G$^{iBu}_{px}$)$_2$G$^{iBu}_{px}$T$_{px}$C$^{Bz}_{px}$-G$^{iBu}_{px}$A$^{Bz}_{px}$C$^{Bz}_{px}$T$_{px}$A$^{Bz}_{px}$A$^{Bz}_{px}$C$^{Bz}_{px}$G$^{iBu}_{px}$C$^{Bz}_{px}$A$^{Bz}_{px}$-G$^{iBu}_{px}$ TOCO—〰— (Ps)] was synthesized.

E. Compound (5) [Synthesis of NH$_2$—R$^1$—$_p$(N$_p$)$_{m+n}$OH]

Example 5 - 1

Figure 4:
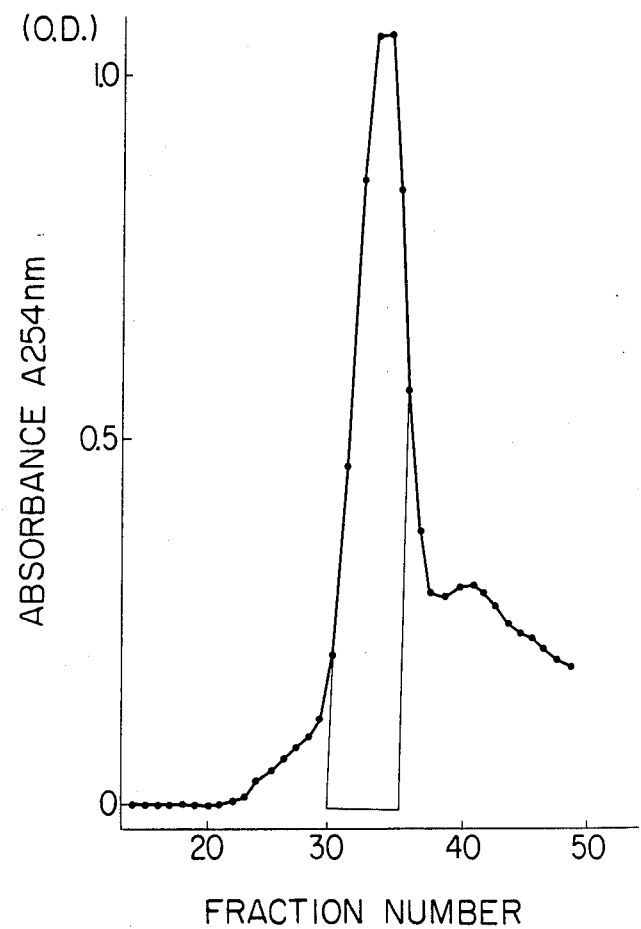

The compound (4 - 1) [Tra—NH—Hex—$_{px}$(A$^{Bz}_{px}$)$_{14}$A$^{Bz}$ —OCO—〰— (Ps)] (15 mg) was sampled in a centrifugal precipitating tube, and a solution of 0.5 M TMG-Oxime in pyridine—H$_2$O (9:1 v/v) (100 ml) was added thereto, the mixture then being left to stand at room temperature for 24 hours. Then, after addition of conc. ammonia water (2.5 ml) thereto, the mixture was left to stand in a sealed state at 50° C. overnight. The resin was filtered off, and the filtrate was concentrated, dissolved in water and extracted three times with ether. The aqueous layer was concentrated and thereafter subjected to desalting purification through Sephadex G - 50 (1.5×120 cm) (eluant: 50 mM TEAB buffer, pH 7.5). The elution pattern is shown in FIG. 4.

Figure 7:
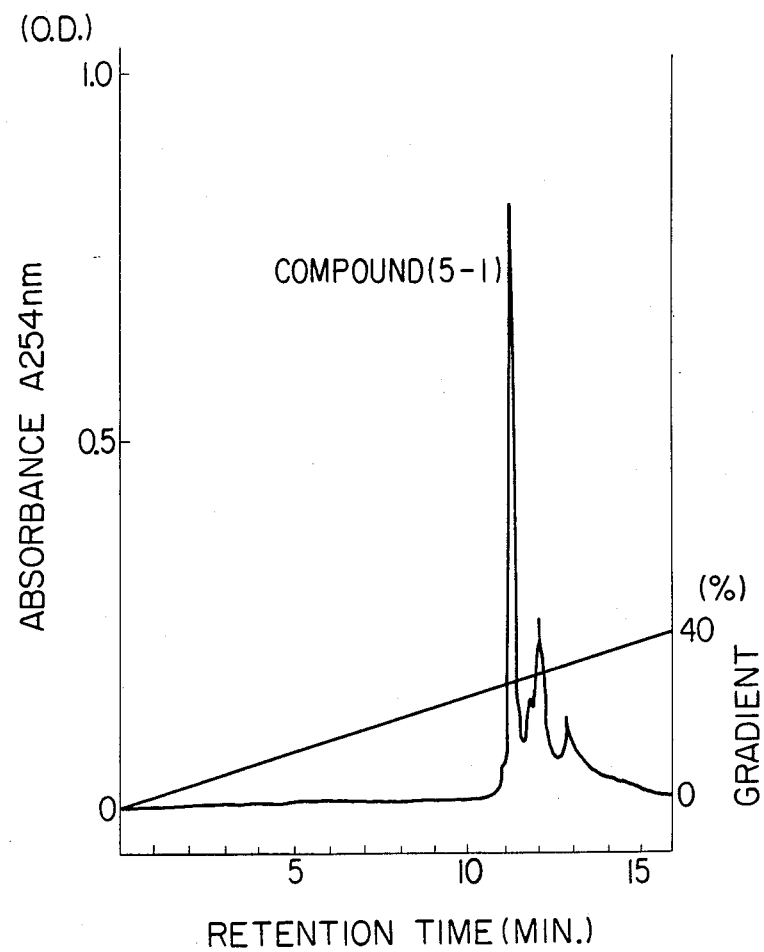
Figure 8:
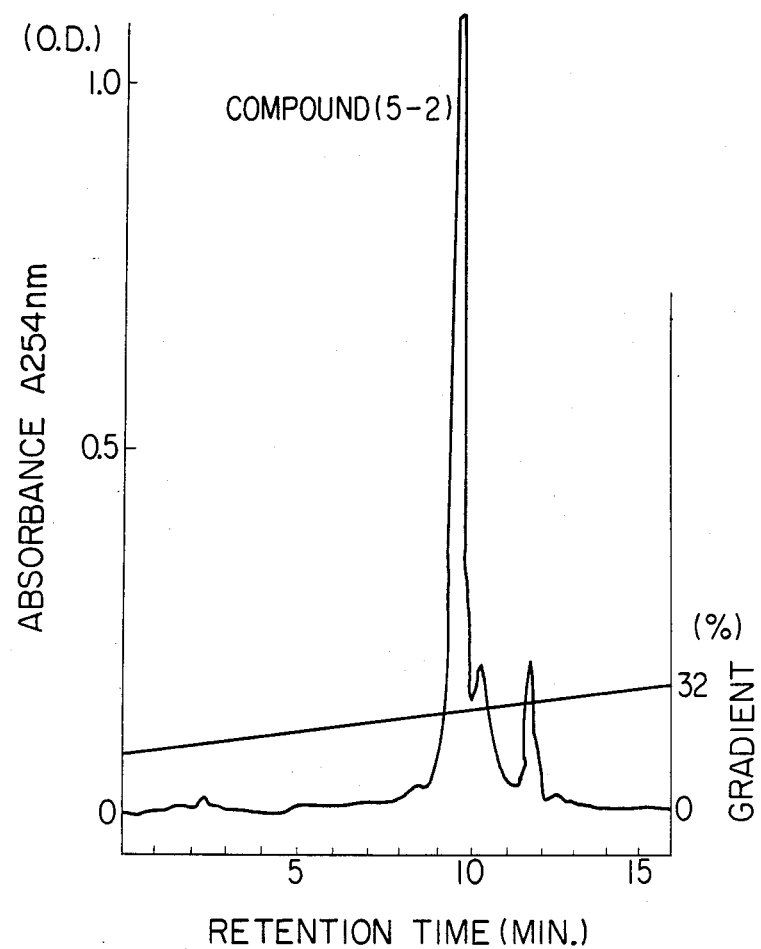

The peaks were collected and concentrated, and the purity of the compound (5 - 1) obtained was assayed by HPLC (μ-Bondapak C18). Its elution pattern is shown in FIG. 7.

Example 5 - 2

Figure 5:
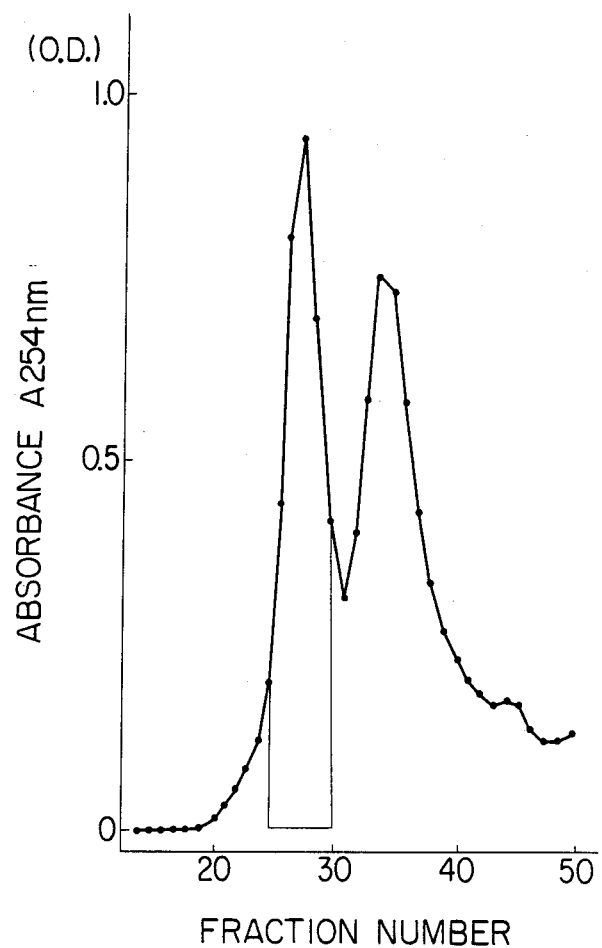

Similarly as in Example 5 - 1, the compound (4 - 2) was deprotected to synthesize the compound (5 - 2) [NH$_2$—Hex—$_p$(T$_p$)$_{14}$TOH. Its elution pattern is shown in FIG. 5 and FIG. 7.

Example 5 - 3

Similarly as in Example 5 - 1, the compound (4 - 3) was deprotected to synthesize the compound (5 - 3) [NH$_2$—Hex—$_p$(A$_p$)$_{11}$AOH].

Example 5 - 4

Figure 6:
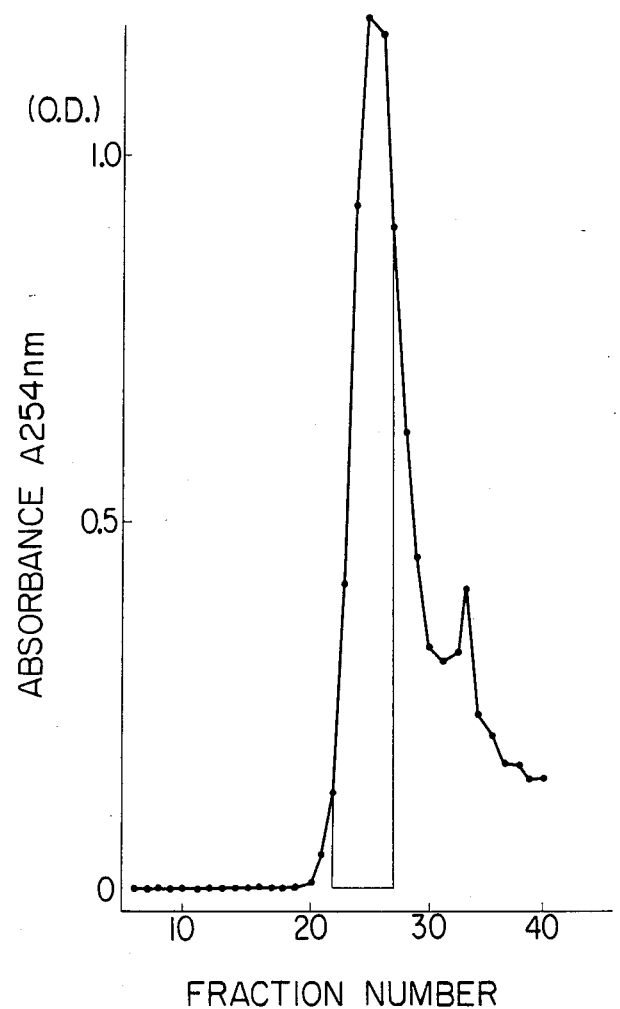
Figure 9:
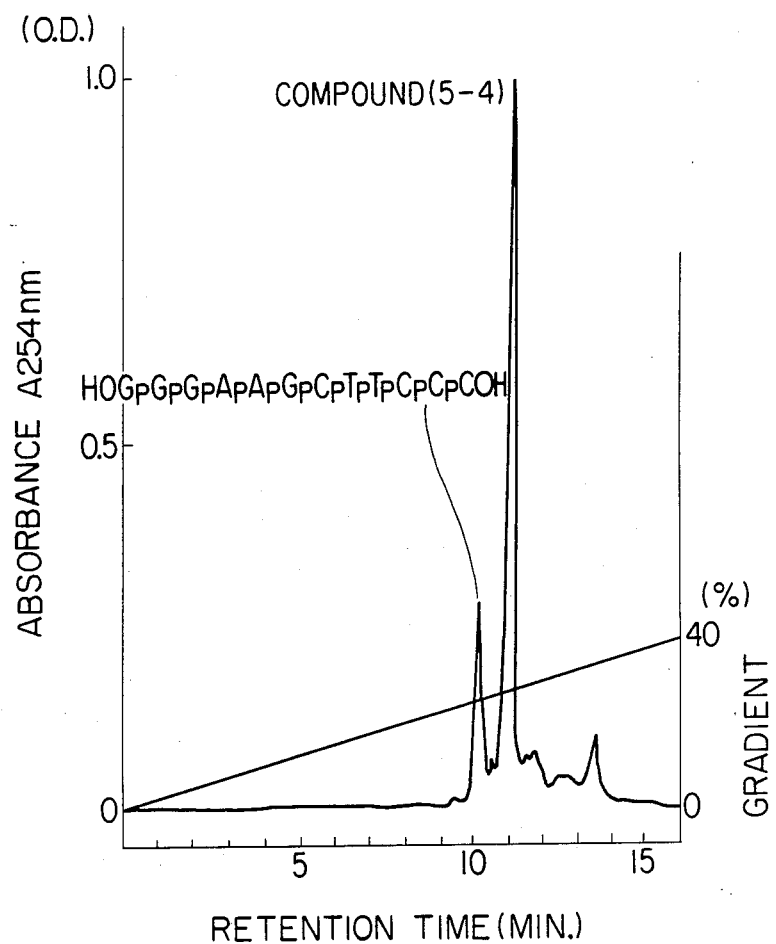

Similarly as in Example 5 - 1, the compound (4 - 4) was deprotected to synthesize the compound (5 - 4) [NH$_2$—Hex—$_p$(T$_p$)$_2$G$_p$G$_p$G$_p$A$_p$A$_p$G$_p$C$_p$T$_p$T$_p$C$_p$C—$_p$COH]. Its elution pattern is shown in FIG. 6 and in FIG. 9.

Example 5 - 5

Similarly as in Example 5 - 1, the compound (4 - 6) was deprotected to synthesize the compound (5 - 5) [NH$_2$—Pen—$_p$(G$_p$)$_2$G$_p$A$_p$A$_p$G$_p$C$_p$T$_p$T$_p$T$_p$C$_p$A$_p$C$_p$G$_p$-T$_p$A$_p$AOH].

Example 5 - 6

Similarly as in Example 5 - 1, the compound (4 - 7) was deprotected to synthesize the compound (5 - 6) [NH$_2$—Pen—$_p$(G$_p$)$_2$G$_p$T$_p$C$_p$G$_p$A$_p$C$_p$T$_p$A$_p$A$_p$C$_p$G$_p$-C$_p$A$_p$G$_p$TOH].

F. Compound (6) [Synthesis of [Sepharose]—NH—R$^1$—$_p$(N$_p$)$_{m+n}$—NOH]

Example 6 - 1

(1) Reagent:
BrCN-activated Sepharose 4B (40 mg)
Compound (5 - 1) [NH$_2$—Hex—$_p$(A$_p$)$_{14}$AOH (4.0 OD)

(2) Reaction:
The BrCN-activated Sepharose 4B was sampled (in the amount shown above), washed with 1 mM—HCl and further with a solution of 0.5 M—NaCl and 0.1 M—NaHCO$_3$ (pH 8.3), and the compound (5 - 1) (in the amount shown above) in a solution of 0.5 M-NaCl and 0.1 M—NaHCO$_3$ (pH 8.3) (200 μl) was added thereto. While under gentle stirring, the reaction was carried out overnight at room temperature. After the reaction, the mixture was subjected to filtration, and the resin was washed with 10 mM-Tris-HCl (pH 7.5) and 0.5 M-NaCl, 10 mM-Tris-HCl (pH 7.5).

(3) Assay of adsorption capacity:
A half amount (20 mg) of this resin was sampled, and affinity chromatography was conducted with the use of synthetic tridecathymidylic acid for assay of the adsorption amount.

Adsorption amount: 1.14 OD/20 mg resin (0.057 OD/mg) (FIG. 10)

(4) Determination of the binding site:
In place of the compound (6 - 1), tridecaadenyl (HO-/A$_{13}$) (crude product) was employed to carry out a similar operation. Substantially no binding was found, and none was detected when adsorption capacity was assayed.

The results of the affinity chromatography column are shown in FIG. 11, which indicates that the adsorption capacity is substantially 0 OD/15 mg (0 OD/mg).

(5) Conclusion:
From the above results, it can be appreciated that no reaction occurs at all on the amino group at the adenine moiety. Therefore, bonding of the compound (6 - 1) to the carrier may be said to have occurred entirely at the amino group extended from the 5'-phosphate group.

Example 6 - 2

(1) Reagent:
Activated CH-Sepharose 4B (30 mg)
Compound (5 - 1) [NH$_2$—Hex—$_p$(A$_p$)$_{14}$AOH](4.0 OD)

(2) Reaction and assay of adsorption capacity:
The activated CH-Sepharose 4B (in the amount shown above) was sampled and washed thoroughly with 1 mM HCl. After the resin was washed quickly with 0.5 M-NaCl, 0.1 M-NaHCO (pH 8.3), the compound (5 - 1) (in the amount shown above) in a solution of 0.5 M-NaCl and 0.1 M-NaHCO$_3$ (pH 8.3) (160 μl ) was added thereto, and the reaction was carried out under gentle shaking at room temperature for 3 hours. After the reaction, the mixture was filtered, and the resin was washed with 10 mM-Tris-HCl (pH 7.5) and 0.5 M-NaCl, 10 mM-Tris-HCl (pH 7.5).

Figure 12:
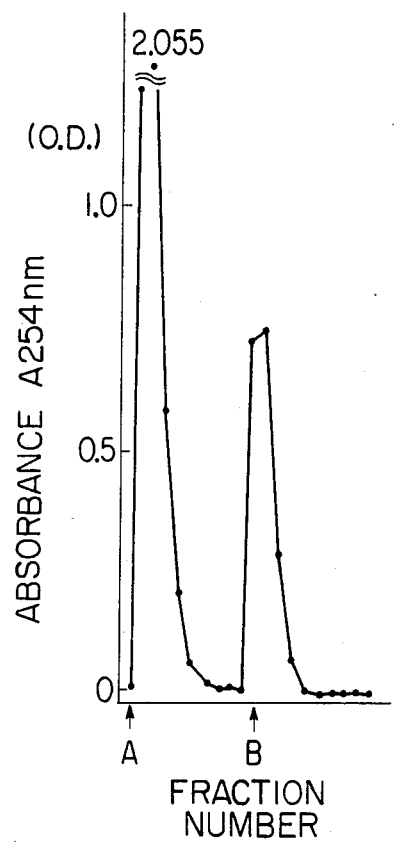

For the resin, the adsorption amount was determined with the use of tridecathymidylic acid and calculated similarly as in Example 6 - 1 (FIG. 12).

Adsorption amount: 0.62 OD/15 mg (0.042 OD/mg)

(3) Determination of binding site:
Adsorption capacity was assayed by carrying out the same reaction as in Example 6 - 1.

Adsorption capacity: substantially 0 OD/15 mg (0 OD/mg)

(4) Conclusion:

Similarly as in Example 6 - 1, binding of 0.042 OD/mg may be said to have occurred entirely at the amino groups extended from the 5'-phosphate group.

Commercially available oligo(dA)-cellulose are said to be bound at the base moiety of adenine, but under the condensing conditions employed, it appears that binding at the adenine base moiety, considered as one possibility, did not really occur at all.

Example 6 - 3

(1) Reagent:
BrCN-activated Sepharose 4B (30 mg)
Compound (5 - 2) (3.43 OD)
$HOT_{13}$ (2.47 OD)

(2) Reaction and assay of the amount bound:

From the results in Example 6 - 1, the oligothymidylic acid ($HOT_{13}$) having no amino group was considered to be further less reactive than oligoadenylic acid ($HOA_{13}$) and unreactive with BrCN-activated Sepharose, and, therefore, for making easier analysis by HPLC, the reaction was carried out with addition of $HOT_{13}$ as internal reference substance.

The reaction was carried out according to the procedure in Example 6 - 1.

From the HPLC pattern of the solution before the reaction, the compound (5 - 2) was found to be about 3.2 OD, $HOT_{13}$ about 2.1 OD and unknown substances about 0.6 OD (5.9 OD as total), but after the reaction the compound (5 - 2) was found to be about 2.1 OD, $HOT_{13}$ about 2.0 OD and unknown substances about 0.5 OD (4.9 OD as total) (FIG. 14), indicating that most of the Sepharose reacted with the compound (5 - 2).

Bound amount: 1.1 OD/30 mg (0.037 OD/mg).

(3) Assay of adsorption capacity:

Adsorption capacity was assayed through an affinity column with the use of $dA_{11}$ (crude product, containing 56% impurities).

Figure 15A:
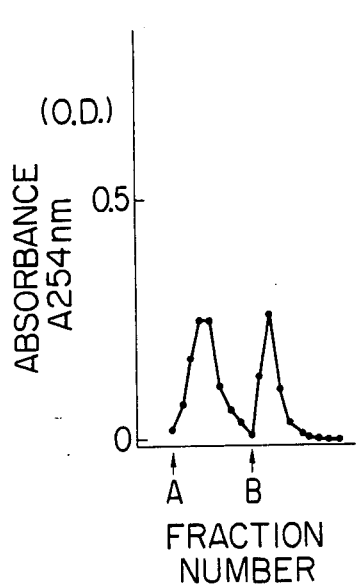

(1) As a result of applying crude $dA_{11}$ (0.55 OD, $dA_{11}$=corresponding to 0.24 OD), only the desired product can be purified and substantially completed (FIG. 15(A)).

Non-adsorbed portion : 0.34 OD
Adsorbed portion: 0.23 OD (2) As the result of adsorption and elution of crude $dA_{11}$ (0.95 OD, $dA_{11}$=corresponding to 0.41 OD), the non-adsorbed portion was 0.73 OD and the adsorbed portion 0.27 OD. As a consequence, the column employed was found to have an adsorption capacity of 0.27 OD, which was about a half of the bound amount calculated from HPLC. This may be considered to be a loss during recovery of the reaction mixture, and it can be explained if the residual OD after crosslinking is considered to have been about 5.2 OD.

Figure 16:
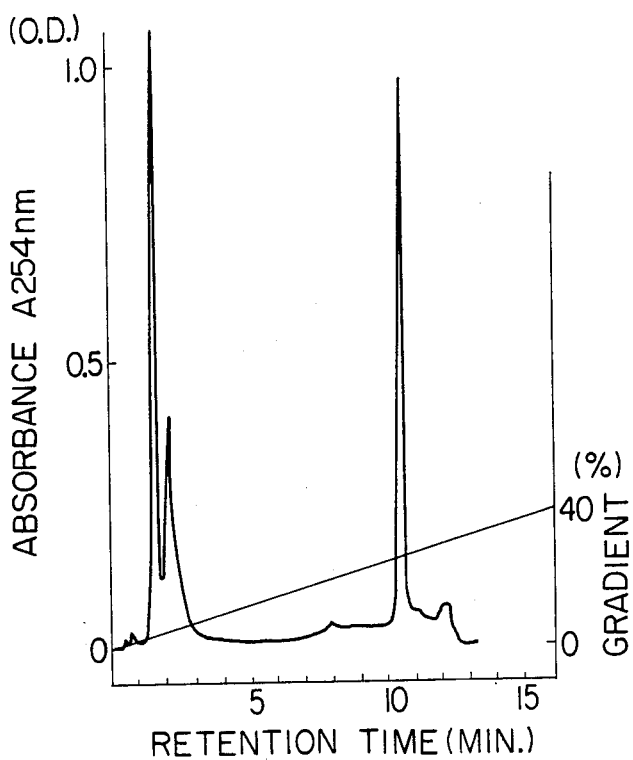

The HPLC pattern at the adsorbed portion is shown in FIG. 16. It can be seen that this $dA_{11}$ is very pure.

(3) Among the above non-adsorbed portions (0.73 OD, $dA_{11}$=0.15 OD), the portion of 0.31 OD ($dA_{11}$ corresponding to 0.06 OD) was eluted again through the column. The non-adsorbed portion was 0.28 OD and the adsorbed portion 0.05 OD.

Figure 17:
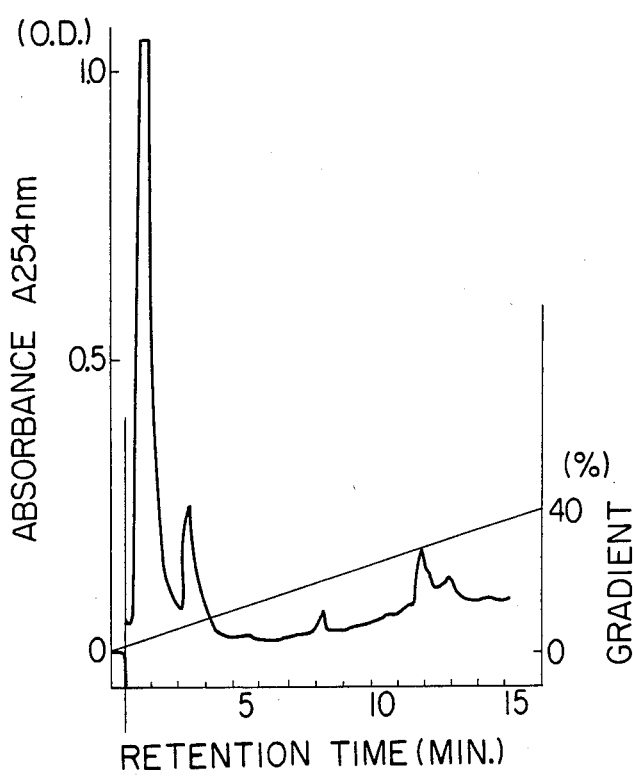

From the HPLC pattern of the non-adsorbed portion, it can be seen that the non-adsorbed portion contained no $dA_{11}$ whatsoever (FIG. 17).

Figure 15B:
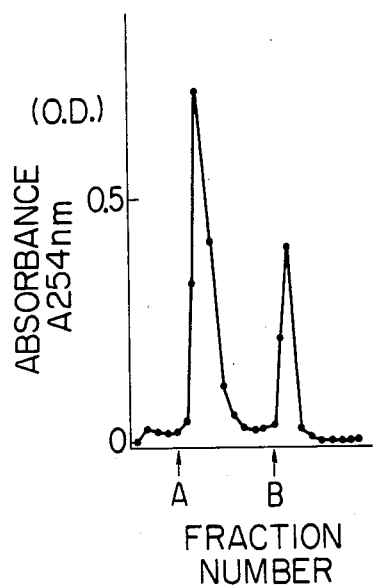
Figure 15C:
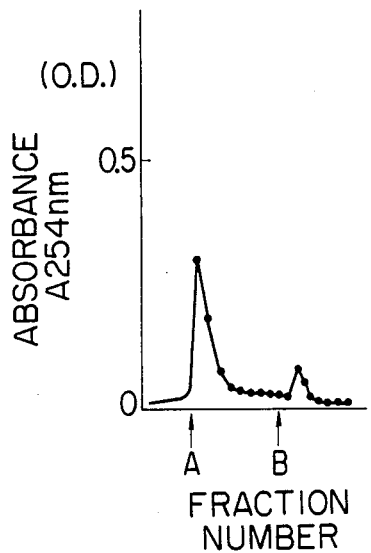

The results of the above chromatography are listed in FIG. 15.

Examples 6 - 4 to 6 - 8

Figure 18A:
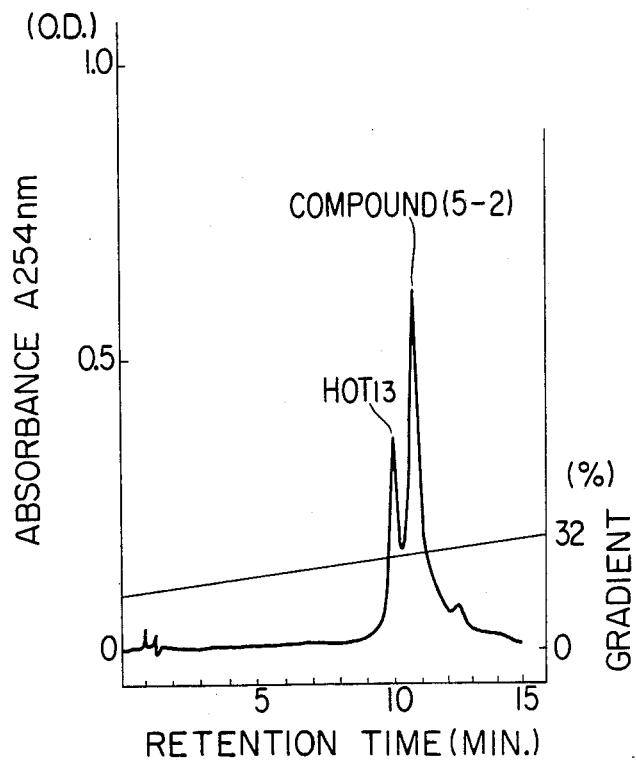
Figure 18B:
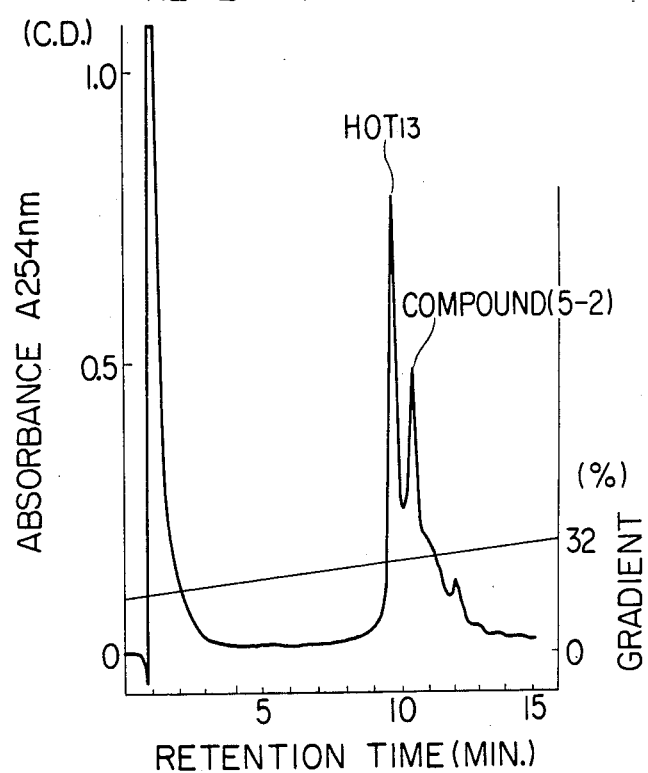

A procedure similar to Example 6 - 3 was carried out to obtain the results shown in Table 6 shown below. The results in Example 6 - 4 corresponding to those in FIG. 14 in Example 6 - 3 are also shown in FIG. 18.

Comparative Example 1

(1) Resin:
Commercially available oligo(dA)-cellulose (P-L Biochemicals Lot No. 115577)

(2) Assay of adsorption capacity:

The above resin was sampled in an amount of 20 mg and, after being caused to swell with a 0.5 M-NaCl, 10 mM-Tris-HCl (pH 7.5) solution, was packed in a column and thereafter washed with 10 mM-Tris-HCl (pH 7.5) and 0.5 M-NaCl, 10 mM-Tris-HCl (pH 7.5) solutions. For this column, the adsorption capacity was assayed with the use of a synthetic tridecathymidylic acid ($HOT_{13}$).

Eluant: 10 mM Tris-HCl (pH 7.5)
One fraction: 15 droplets (350 µl)

(1) When 2.1 ml of a solution of $HOT_{13}$ with 1.33 OD in 0.5 M-NaCl, 10 mM-Tris-HCl solution was applied, almost no adsorption thereof occurred.

(2) The eluate from the above (1) was recovered and adsorption was attempted again. No adsorption whatsoever occurred.

Figure 19A:
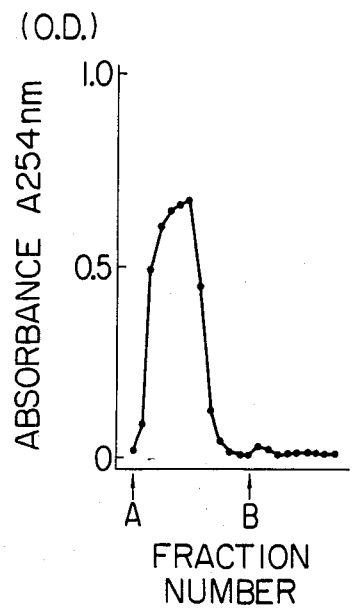
Figure 19B:
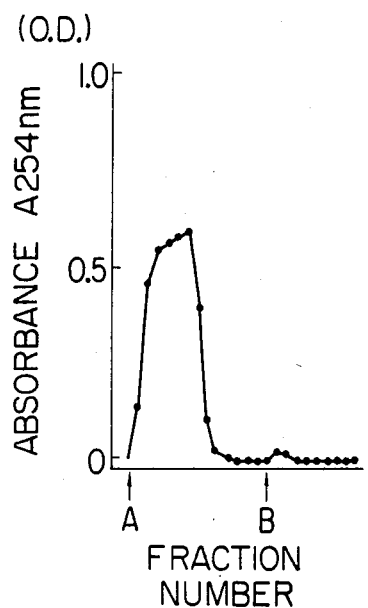
Figure 19C:
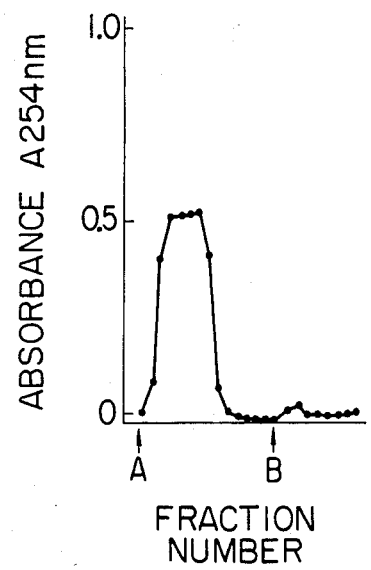
Figure 20A:
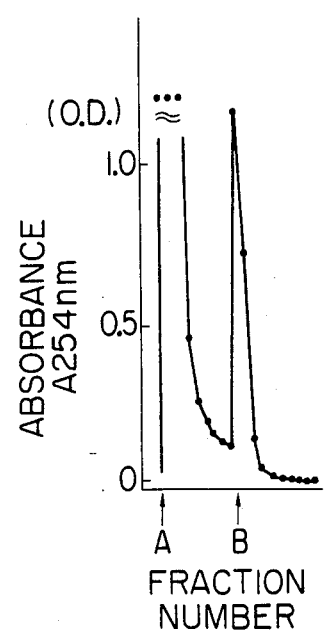
Figure 20B:
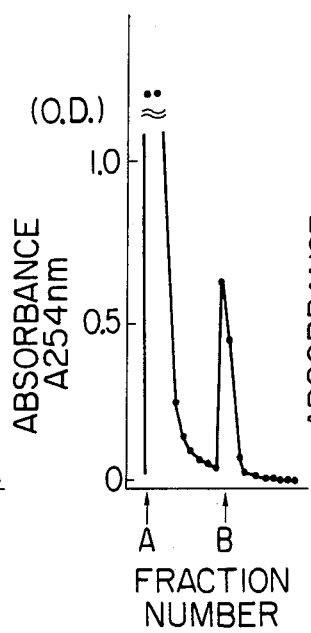
Figure 20C:
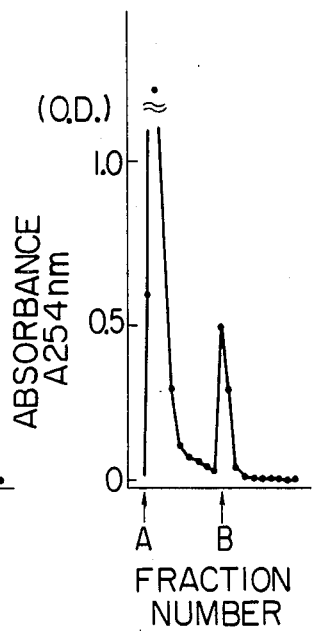
Figure 20D:
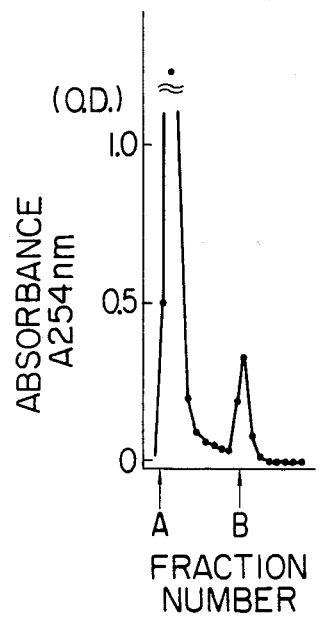
Figure 20E:
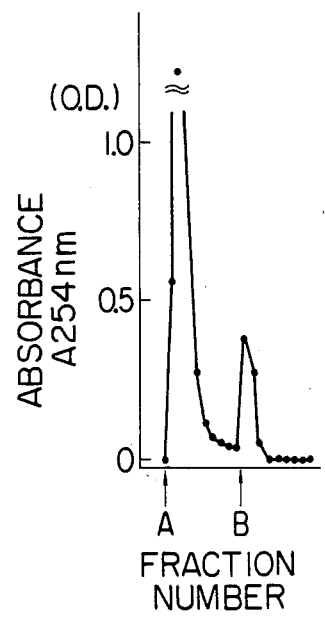

(3) A column was newly prepared, and assay was similarly conducted. With regard to the above three points, the results are shown in FIG. 19.

(3) Conclusion:

In spite of its being a commercially available resin for adsorption, it has almost no adsorption capacity.

It has been known in the art that there is no oligo(-dA)-cellulose of good quality, as compared with oligo(dT)-cellulose, and these results may be construed to support this fact.

Comparative Example 2

(1) Resin:
Commercially available oligo(dT)-cellulose (P-L Biochemicals Lot No. 675130)

(2) Assay of adsorption capacity:

Similarly as in Comparative Example 1, assay was conducted with the use of $HOA_{13}$. The results calculated from FIG. 20 are shown in Table 5 below.

TABLE 5

| | Amount of vital test sample (µl) | Amount adsorbed (OD/20 mg) | Adsorption capacity (OD/mg) |
| --- | --- | --- | --- |
| FIG. 20-A | 4.3 OD/200 | 0.73 | 0.037 |
| FIG. 20-B | 3.0 /350 | 0.41 | 0.021 |
| FIG. 20-C | 1.5 /700 | 0.31 | 0.016 |
| FIG. 20-D | 1.7 /350 | 0.19 | 0.010 |
| FIG. 20-E | 1.8 /350 | 0.26 | 0.013 |

(3) Conclusion:

Depending on the difference in amount or concentration of the vital test sample, or by repeating adsorption and elution, the adsorption capacity varies, whereby no reproducible result can be obtained.

The above results are summarized in Table 6.

TABLE 6

Figure 13:
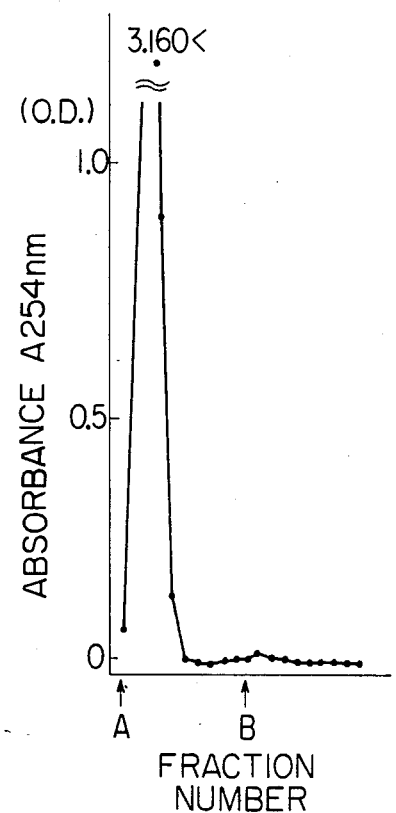
Figure 14A:
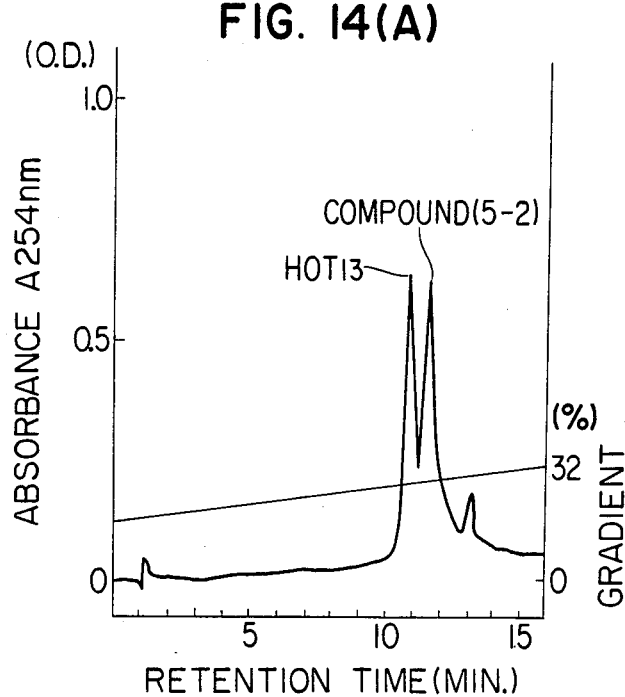
Figure 14B:
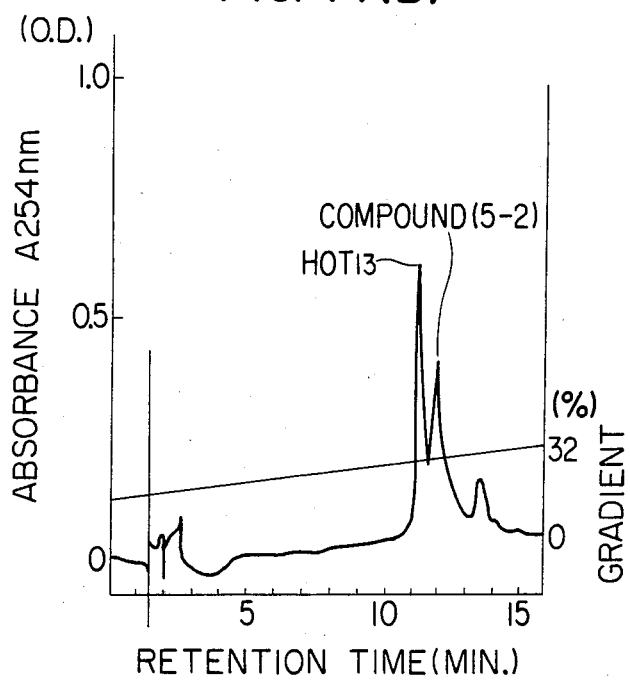

| | Sample | | Bound amount | | Adsorption capacity | | |
|---|---|---|---|---|---|---|---|
| | Carrier | Oligo (dN) | OD/mg | HPLC | Test sample | OD/mg | Column |
| Example | | | | | | | |
| 6-1 | a | Compound(5-1) | | | $HOT_{13}$ | 0.057 | FIG. 10 |
| 6-1 | a | $HOA_{13}$ | | | $HOT_{13}$ | 0 | FIG. 11 |
| 6-2 | b | Compound(5-1) | | | $HOT_{13}$ | 0.047 | FIG. 12 |
| 6-2 | b | $HOA_{13}$ | | | $HOT_{13}$ | 0 | FIG. 13 |
| 6-3 | a | Compound(5-2) | 0.037 | FIG. 14 | $HOA_{13}$ | 0.037 | FIG. 15 |
| 6-4 | b | Compound(5-2) | 0.049 | FIG. 18 | $HOA_{13}$ | 0.049 | |
| 6-5 | a | Compound(5-4) | 0.004 | | * | ** | |
| 6-6 | b | Compound(5-4) | 0.016 | | * | ** | |
| 6-7 | a | Compound(5-5) | 0.024 | | *** | | |
| 6-8 | a | Compound(5-6) | 0.035 | | **** | | |
| Commercial product | | | | | | | |
| 1 | c | | — | | $HOT_{13}$ | 0 | FIG. 19 |
| 2 | d | | — | | $HOA_{13}$ | 0.010 –0.037 | FIG. 20 | a = BrCN-activated Sepharose 4B;
b = activated CH-Sepharose 4B
(a and b are produced by Pharmacia Fine Chemicals, U.S.A.);
c = Oligo (dA)-cellulose (Lot No. 115577);
d = Oligo (dT)-cellulose (Lot No. 675130);
*$5'HOG_pG_pG_pA_pA_pG_pC_pT_pT_pC_pC_pCOH^{3'}$;
**not adsorbed due to self-complementarity, unmeasurable;
***$5'HOT_pT_pA_pC_pG_pT_pG_pA_pA_pA_pG_pC_pT_pT_pCOH^{3'}$
****$5'HOA_pC_pT_pG_pC_pG_pT_pT_pA_pG_pT_pC_pG_pA_pCOH^{3'}$

What is claimed is:

1. An oligonucleotide derivative of the formula:

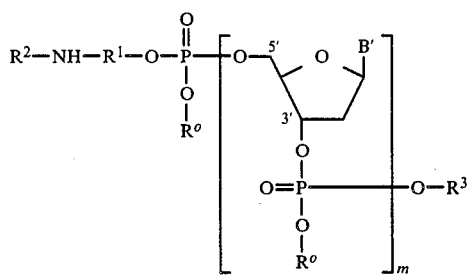

wherein
$R^o$ is selected from the group consisting of o-chlorophenyl and p-chlorophenyl;
$R^1$ is a $C_2$-$C_6$ alkylene;
$R^2$ is selected from the group consisting of trifluoroacetyl and o-nitrophenyl sulphenyl;
$R^3$ is cyanoethyl;
B' is the same or different and is selected from the group consisting of $N^6$-benzoyladenin-9-yl, $N^4$-benzoylcytosin-1-yl, $N^2$-isobutyrylguanin-9-yl, and thymin-1-yl; and m is 2.

2. An oligonucleotide of the formula:

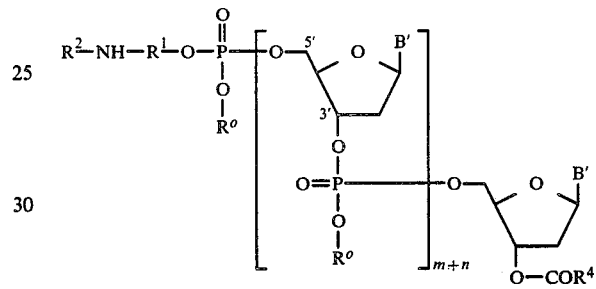

wherein
$R^o$ is selected from the group consisting of o-chlorophenyl and p-chlorophenyl;
$R^1$ is a $C_2$-$C_6$ alkylene;
$R^2$ is selected from the group consisting of trifluoroacetyl and o-nitrophenyl sulphenyl;
B' is the same or different and is selected from the group consisting of $N^6$-benzoyladenin-9-yl, $N^4$-benzoylcytosin-1-yl, $N^2$-isobutyrylguanin-9-yl, and thymin-1-yl;
$R^4$ is polystyrene;
m is 2; and
n is 1–12.

3. An oligonucleotide of the formula:

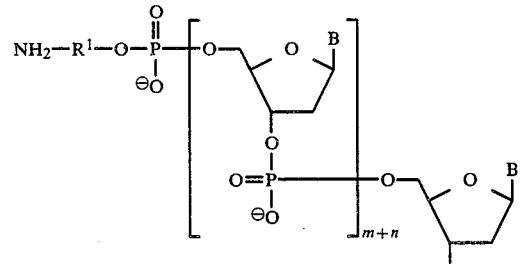

wherein
$R^1$ is a $C_2$-$C_6$alkylene;
B is the same or different and is selected from the group consisting of adenin-9-yl, guanin-9-yl, cytosin-1-yl and thymin-1-yl;
m is 2; and
n is 1–12.

* * * * *